United States Patent [19]

Rainey et al.

[11] 4,292,848
[45] Oct. 6, 1981

[54] WALKING-GATE ULTRASONIC FLAW DETECTOR

[75] Inventors: J. Montgomery Rainey, Dayton; Francis M. Taylor, Xenia, both of Ohio

[73] Assignee: Systems Research Laboratories, Inc., Dayton, Ohio

[21] Appl. No.: 139,537

[22] Filed: Apr. 11, 1980

[51] Int. Cl.³ ............................................. G01N 29/04
[52] U.S. Cl. ......................................... 73/602; 73/620
[58] Field of Search .................. 73/602, 609, 610, 614, 73/620

[56] References Cited
U.S. PATENT DOCUMENTS 3,977,236   8/1976   Raatz et al. ........................... 73/614

*Primary Examiner*—Anthony V. Ciarlante
*Attorney, Agent, or Firm*—Biebel, French & Nauman

[57] ABSTRACT

A microprocessor-based ultrasonic inspection system reliably detects fatigue cracks smaller than 0.030 inch under installed fasteners by means of a unique signal-processing method. The signal-processing used in this invention takes advantage of the fact that crack signals "walk" in time as a transducer moves around a fastener. Bolt size, scan depth, and angle of incidence of an ultrasonic shear wave are used to determine the "walk rate" of a defect in the inspection zone. With this geometric information, the signal-processing technique will enhance any pulse-echo return "walking" at the computed walk rate, and thus significantly improve the ratio of crack signal to other signal sources in the material.

4 Claims, 25 Drawing Figures

FIG-11
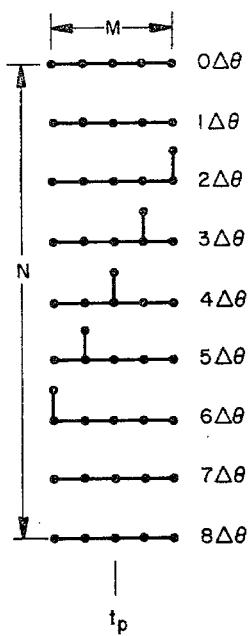
a) CONTENTS OF THE SAMPLING GATE AT EACH $\Delta\theta$ LOCATION
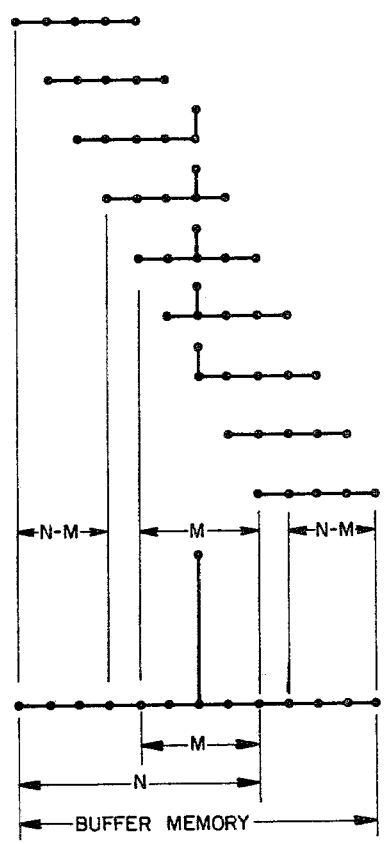
b) SHIFT AND ADD
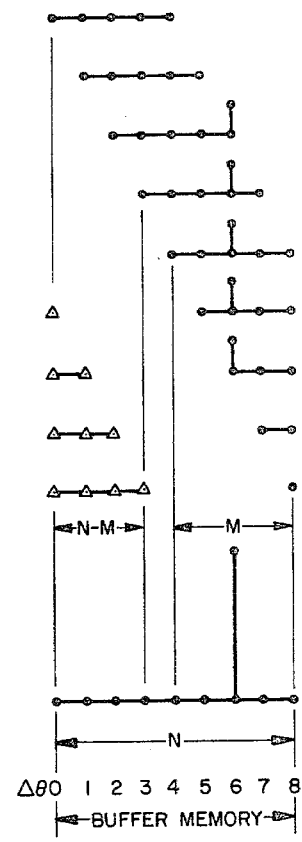
c) COMPLETE PARTIAL SUMS
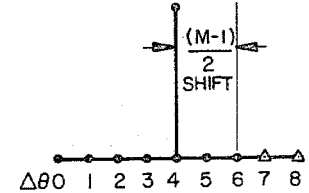
d) CIRCULAR SHIFT

WALKING-GATE ULTRASONIC FLAW DETECTOR

The U.S. Government has rights in this invention pursuant to contract No. F 33615-78-C-5021 awarded by the Department of the Air Force.

BACKGROUND OF THE INVENTION

This invention relates to an ultrasonic flaw detector, and particularly to a flaw detector used in connection with the detection of fatigue cracks associated with fasteners in aircraft wing surfaces.

Fatigue cracks extending from openings in metal surfaces, such as those openings formed to accept fasteners in aircraft wings, will grow when subject to stress. If cracks and other flaws associated with these fasteners in aircraft wings can be detected while they are yet very small, the fastener can be removed, the hole enlarged to remove the flaw, and an oversized fastener installed in its place.

Since fasteners are available in 1/64 inch increments, it would be desirable if fatigue cracks within this size range could be detected. However, cracks of this size are difficult to detect with prior art techniques without also experiencing an unreasonably large false call rate, that is, the detection of apparent cracks or flaws caused by something other than an actual crack or flaw, such as out-of-round holes.

If the crack becomes as large as 0.200 inch, catastrophic failure of the wing could occur. It is not unusual for the prior art devices to reliably detect cracks as small as 0.030 inch, however, detecting cracks as small as 0.010 inch requires the special techniques developed in connection with this invention.

Those experienced with the operation of prior art devices, for example that shown in U.S. Pat. No. 3,977,236, have noted that as an ultrasonic transducer is rotated around the central axis of a fastener, an A-scan presentation of the crack or flaw return signal will apparently move as the transducer is rotated. This moving signal, however, is sometimes masked by other return signals, and therefore very small cracks are frequently undetected.

SUMMARY OF THE INVENTION

This invention relates to a specialized walking gate ultrasonic flaw detector. Ultrasonic return signals from a transducer moving relative to a flaw, are both time-signal averaged and spatial-signal averaged to provide for the detection of flaws as small as 0.010 inch.

In a preferred embodiment of the invention, a pair of ultrasonic transducers are mounted in a scanner and rotated in both the clockwise and counterclockwise direction around the central axis of a fastener. A magnetic centering device is employed to insure that the transducer rotates about the central axis of the fastener. The radial spacing of the transducers from the axis of rotation can be adjusted to accommodate for different fastener sizes, and the angle at which the transducer looks into the material may be adjusted so that flaws in the coutersink region, at the faying surface, or some other location within the material can be detected.

Basically, the transducer is positioned relative to the flaw, a plurality of pulses are transmitted into the material, and the echos from the pulses received and are time-signal averaged. The invention includes gate means so that only those signals received in the time period when the flaws are likely to be returned are analyzed. Within this large gate, the signals are divided into a plurality of segments (64 in the preferred embodiment of the invention) and a number representing the amplitude of the return signal within each of these segments is stored in specified memory locations. Thereafter, the transducer is moved through an incremetal distance which is carefully calculated so that any signals returned to the transducer from a flaw will have moved the equivalent of one memory space. The transducer is then again pulsed a plurality of times, and the return signal time-signal averaged, and those signals within the gate are stored again in the memory; however, this time, the signals will be moved one memory position so that the numbers accumulated in the memories represent the amplitudes of the detected signal within the same volume of material undergoing investigation.

All of the above steps are repeated a number of times until the fastener has been completely encircled at least once. In the preferred embodiment, a second transducer is also employed, and the scanning head rotated in the opposite direction to insure that the area within investigation has been completely scanned for flaws.

By using the spatial-signal averaging or walking gate technique of this invention, random noise will be averaged out, stationary return signals will appear as an offset, and only those signals which appear to walk or move at substantially the calculated rate for the volume of material under investigation.

Accordingly, it is an object of this invention to provide a method of detecting flaws within solid material ultrasonically comprising the steps of: positioning a transducer relative to suspected flaws and transmitting an ultrasonic pulse beam into the material under test; detecting reflected ultrasonic signals within a time period when suspected flaw signals are likely to be returned; dividing the detected signals within said time period into a plurality of segments and measuring the amplitude of each segment; adding a number representing the amplitude of the detected signal for each segment into individual memories; thereafter moving said transducer through an incremental distance such that the transit time of the ultrasonic signal is shortened or lengthened by one time segment with respect to a given spatial location within said material, and then transmitting another pulse into said material; accumulating the numbers representing the amplitude of the detected signal for each segment into said memories after the relative position of said segments and said memories has been shifted in the direction related to the movement of said transducer; repeating the above steps until the transducer has traversed the area of suspected flaws whereby signals received within said time period relating to given spatial locations are accumulated in the memories; and thereafter reading the memories to obtain information regarding the location and magnitude of any flaws within the material.

It is a further object of this invention to provide an apparatus for the ultrasonic detection of flaws located within solid material, said apparatus including; transducer means positioned at an acute angle to the surface for transmitting a narrow beam of ultrasonic energy into the material and for receiving signals reflected from within the material; means for moving said transducer relative to the surface of the material; means for sensing the signals received by said transducer means within the limited period of time reflected signals from flaws within the material are likely to occur; means for dividing said received signals within said period of time into a plurality of equally spaced segments; means for causing said transducer to transmit pulses of ultrasonic energy each time said transducer moves through an increment of distance represented by one of said segments; a plurality of memory means responsive to said transducer means for storing representations of the amplitude of the received signals within each of said segments; means for adding the representations of amplitude of the received signals into corresponding memories within said memory means; and means for interrogating said memories after said transducer has traversed the suspected flaw locations to determine the spatial locations of any flaws detected.

These and other objects of the invention will be apparent from the following description, the accompanying drawings and the appended claims.

BRIEF DESCRIPTION OF THE DRAWINGS

FIGS. 11a-11d are a simplified set of wave forms showing the walking gate process of this invention.

DESCRIPTION OF THE PREFERRED EMBODIMENT

Figure 1:
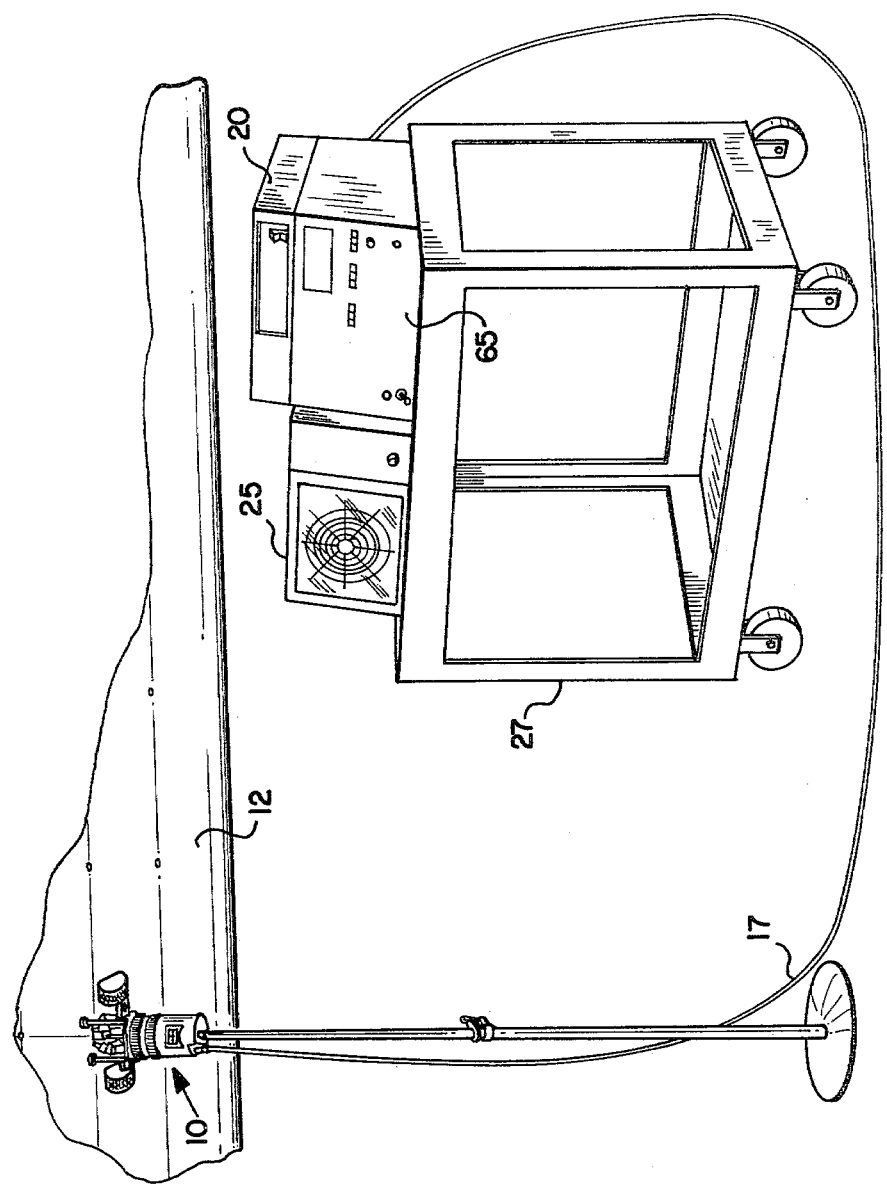
FIG. 1 is a perspective view showing an ultrasonic scanning head positioned adjacent the underneath side of an aircraft wing, and the associated electronic processing console and CRT display.

Referring now to the drawings which show a preferred embodiment of the invention, FIG. 1 illustrates a portable ultrasonic inspection system useful in connection with the detection of fatigue cracks associated with fasteners such as those used in aircraft wings. As shown, the inspection system includes an ultrasonic head assembly 10 supported in position against the underside of an aircraft wing 12 by spring-loaded pole 15 and connected by cable 17 to an electronics package 20 which controls the operation of the head assembly and processes the information obtained therefrom. A display device or cathode ray tube (CRT) 25 may be associated with the electronic package 20 on a cart 27.

Figure 2:
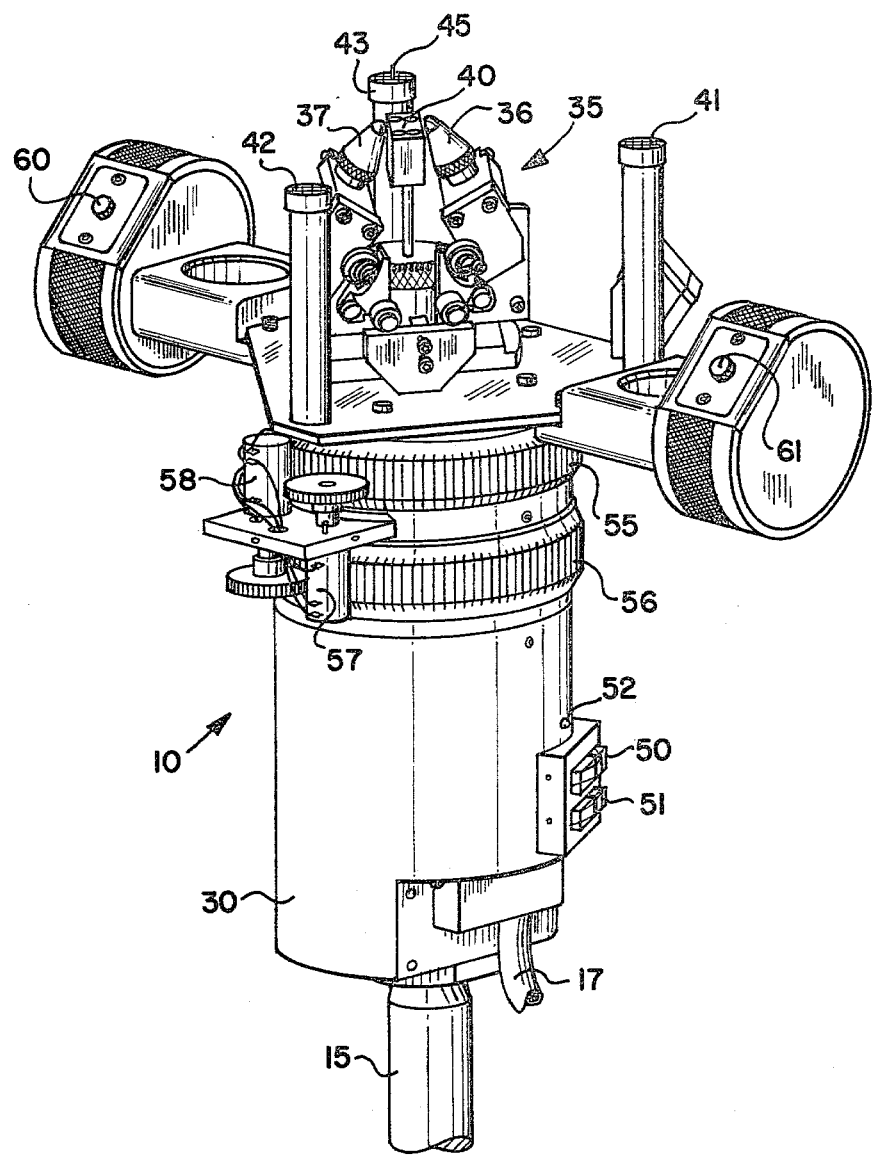
FIG. 2 is a perspective view of the scanner showing the ultrasonic transducers, magnetic centering device, transducer spacing and orientation mechanism and control switches.

The head assembly, shown in detail in FIG. 2, includes a housing 30 provided with a bottom mounted fitting for connection with the pole 15. Within the housing is a stepping motor for rotating a probe assembly 35 including a pair of electronic crack detection probes 36 and 37 about a central axis. Mounted on the axis is an X-Y position sensor 40.

The head assembly 10 is spaced from the wing surface by means of three spacer rods, 41, 42, 43 one of which includes a switch 45 for indicating when the assembly is in place. The position of a fastener with respect to the central axis is detected by the X-Y position sensor, and the position may be indicated by the X position dial 50 and the Y position dial 51 mounted on the housing 30. Proper centering of the head assembly over a fastener will be shown by an indicator lamp 52.

An adjustable ring 55 mounted on the upper portion of the housing may be manipulated by the operator to adjust the spacing of the transducers for the proper bolt diameter. A second ring 56, coaxially spaced and mounted below the first ring sets the depth of the scan, or in other words, properly positions the angle of the transducer to search for flaws at a particular depth below the surface of the wing. The positions of the rings 55 and 56, and thus the spacing and the angle of the transducers, can be read remotely by means of precision potentiometers 57 and 58.

In operation, the head is brought into contact with the wing and supported in place by the spring-loaded pole 15. When in position, the switch 45 will close, and the operator manipulates the head by reference to the X and Y position dials 50 and 51 until the device is properly centered over the fastener as indicated by the lamp 52. The rings 55 and 56 are set for the bolt diameter and the desired scan depth.

The operator then actuates the push-button switches 60 and 61, and the probe assembly 35 will rotate the transducers for at least 360° around the fastener in one direction with transducer 36 being active and then the direction of travel will be reversed so that the transducer 37 can also view the area of the suspected flaws. After the head has rotated about one fastener in both directions, the information regarding suspected flaws is recorded, and the head assembly may then be moved to the next fastener and the inspection process repeated.

Figure 3:
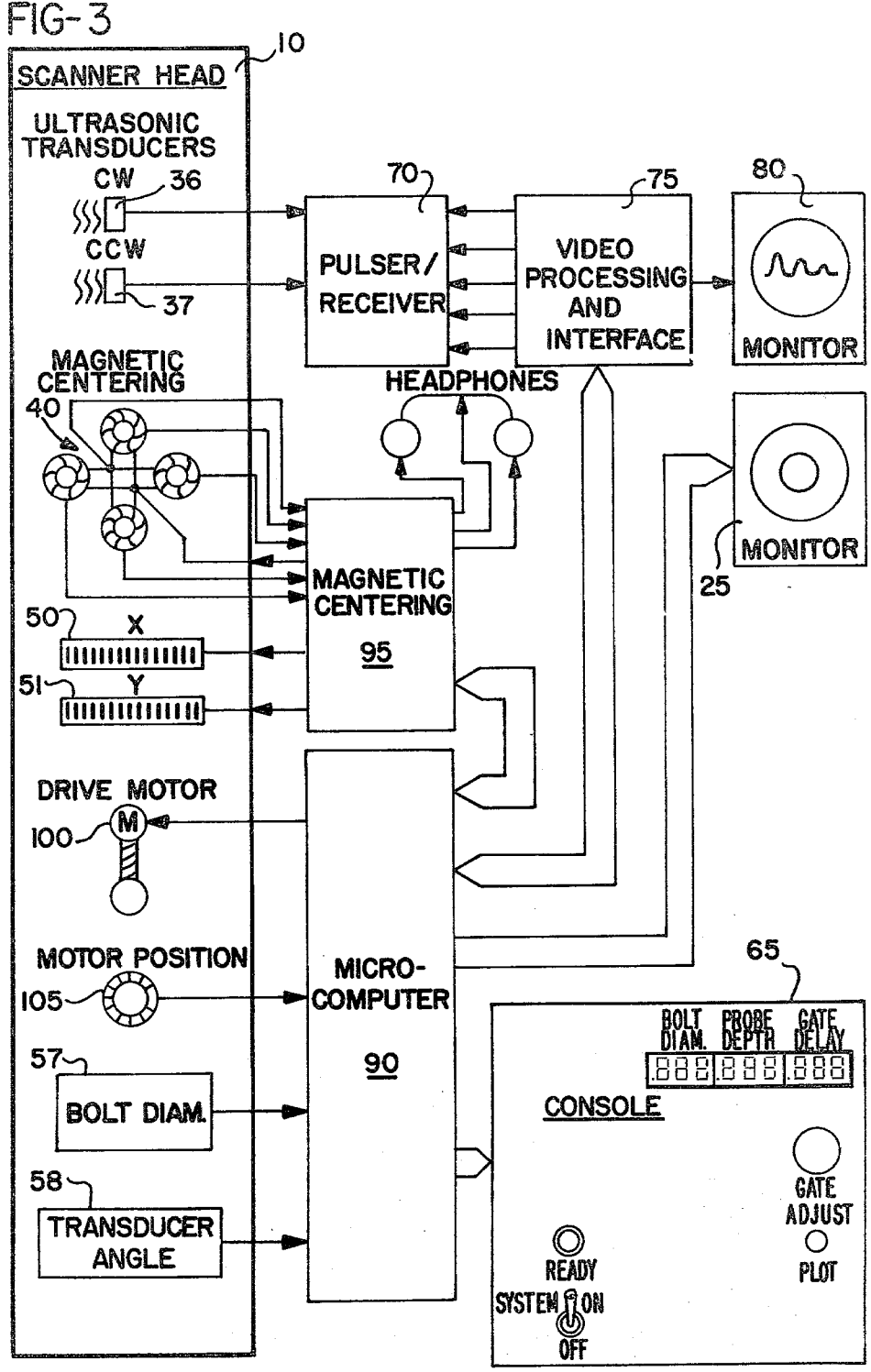
FIG. 3 is a simplified block diagram showing the basic components of the invention and their relationship to each other.

FIG. 3 shows in block diagram form showing the basic components comprising the ultrasonic inspection system. The head assembly 10, as previously explained, includes the ultrasonic transducers 36 and 37. These transducers are connected to a pulse receiver 70, and this device is connected to a video processing and interface circuit 75 having several outputs, one going to a monitor oscilloscope 80, and another to a microcomputer 90.

The x-y position sensors or magnetic centering devices 40 are connected to a magnetic centering circuit 95. This circuit may have an audio output through headphones 96, and also a visual output through the X-position indicator 50 and the Y-position indicator 51 and indicator lamp 52.

The ultrasonic transducers are rotated by means of a stepping motor 100, and the motor position is sensed by a motor position indicator 105 having an output connected to the microcomputer 90.

The microcomputer 90 is connected to a monitor 25, which is preferably an oscilloscope having a plan-position indicator display, and to the display and control panel 65 which contains visual displays for bolt diameter, scan depth, and controls for the operation of the system.

Figure 4:
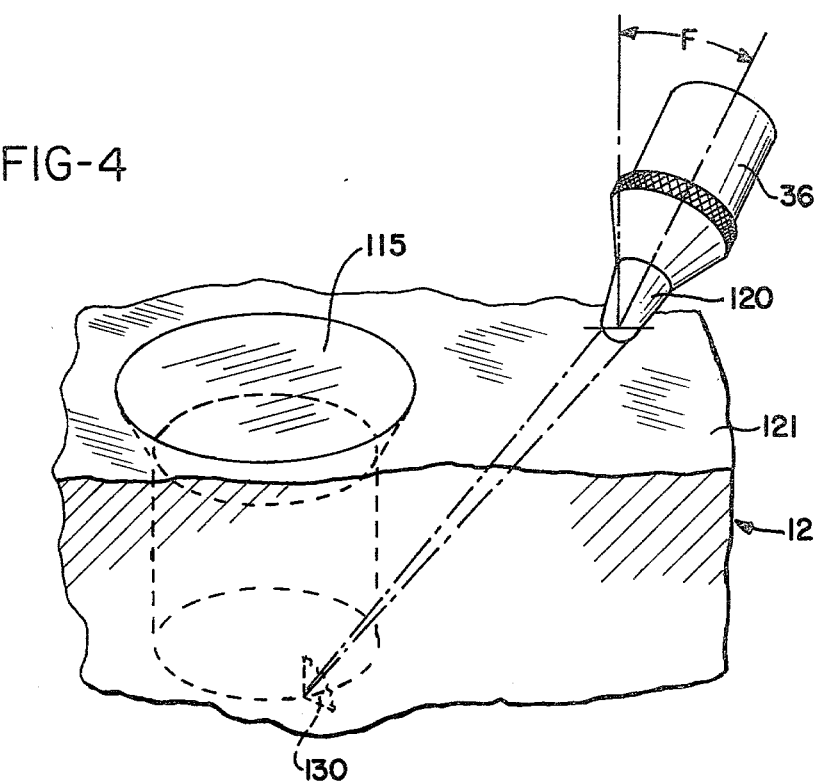
FIG. 4 shows an ultrasonic probe positioned for scanning a defect associated with a fastener.

FIG. 4 shows one of the probes or transducers 36 placed adjacent a fastener 115 installed in a section of aircraft wing 12. The transducer is a highly focused device provided with a water filled boot 120 the end of which engages the outer surface 121 of the wing 12. It or some other fluid coupling is applied to the wing surface. The water column within the boot, the boot tip, and oil film all act to couple the ultrasound into the wing structure. If a fatigue crack 130 at the faying surface 132 is encountered, an ultrasonic pulse will be reflected back along the path of entry.

A receiver peak-detects the amplitude of the return pulse and displays it as an inward deflection on a circular cathode ray tube display, thus indicating the magnitude of the return and the angular position of the defect relative to the scanner. If a defect is detected, the operator next looks at the A-scan, shown by the monitor 80, to determine whether the return pulse "walks in time" as the transducer is rotated about the fastener 115.

This invention employs both time signal averaging and walking-gate spatial averaging to capatalize on the walking effect and to perform the signal processing necessary to filter walking defect returns from time-stationary artifact returns.

This signal-processing technique greatly improves the reliability of ultrasonic circular-bolt-hole scanning by minimizing first-surface and countersink time-stationary returns in addition to increasing spatial resolution and the overall signal-to-noise ratio.

Figure 8:
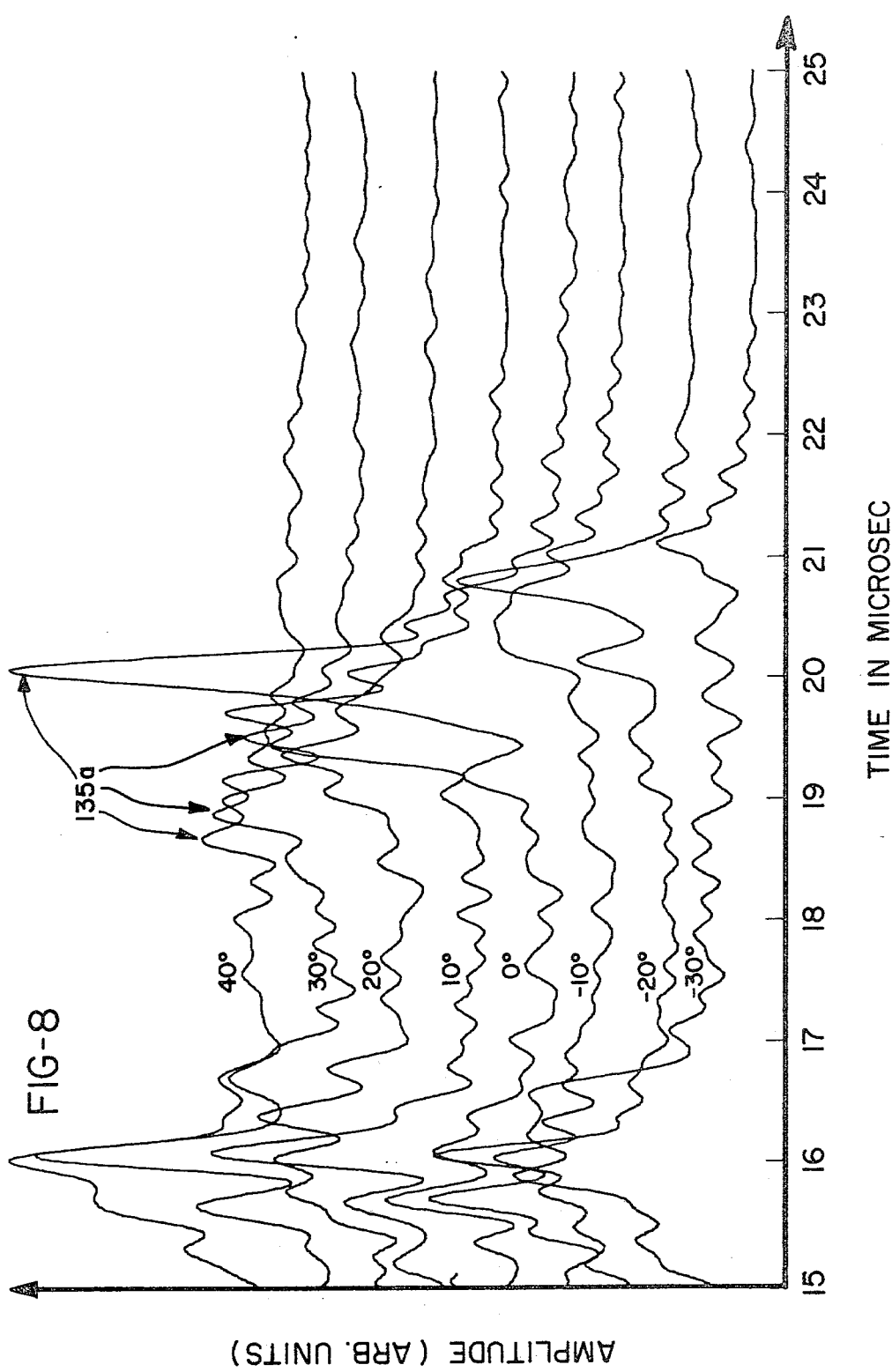
FIGS. 8 and 9 illustrate video A-scan returns from two different sized defects in the counter-sync region in a ½ inch tapered fastener.
Figure 9:
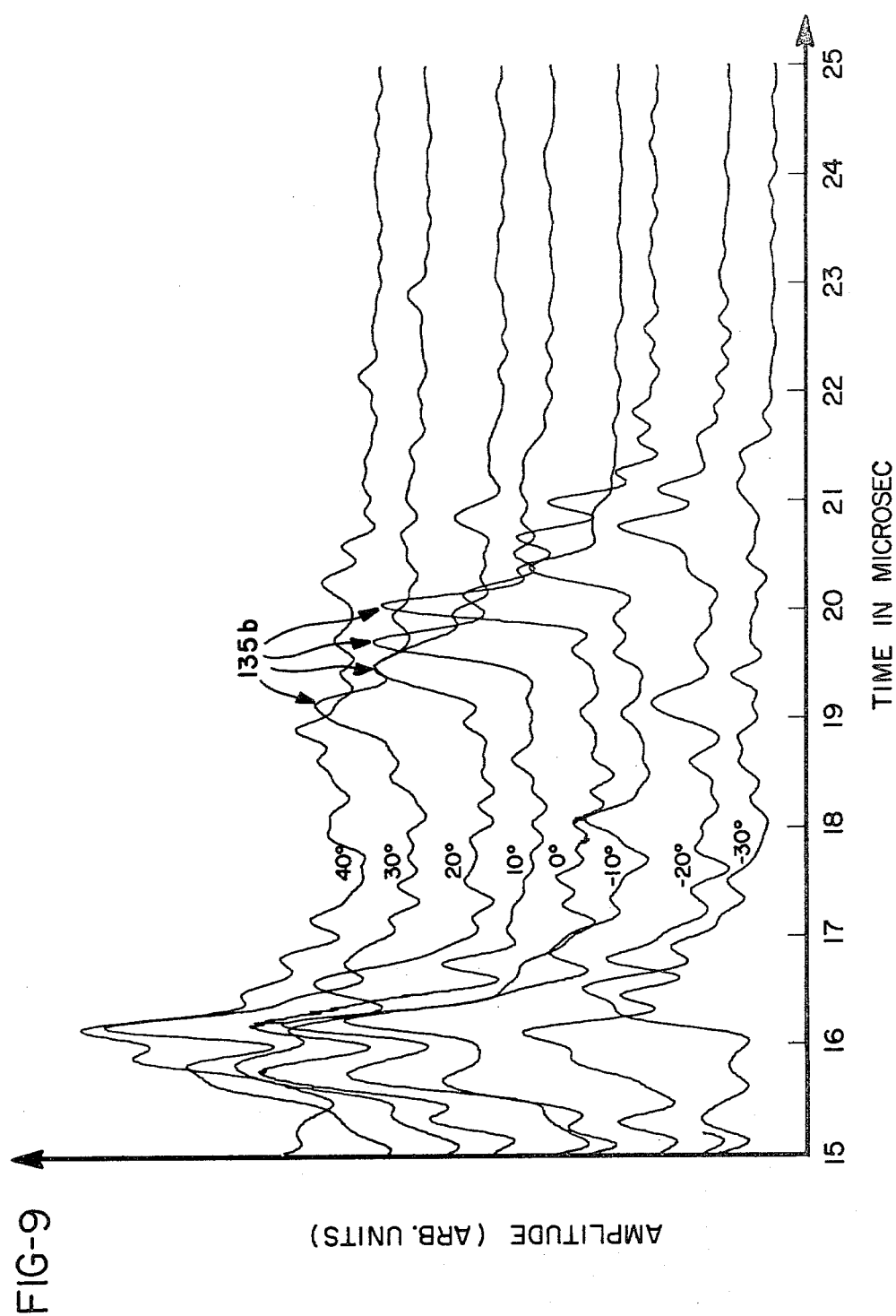

FIGS. 8 and 9 represent, respectively, the video A-scan returns from an 0.080-in. and 0.20-in. quarter-penny EDM notch located in the countersink region of a ¼-in. tapered fastener. The angle of incidence of the ultrasonic transducer is 27°, which yields a refracted shear wave of approximately 75° in the aluminum wing skin. The countersilk region is inspected using direct back-scattering from the defect, with no bounce off the faying surface.

Each A-scan is recorded at a different spatial position relative to the defect. There is a large time-stationary return from the countersink followed by a defect indication 135a, which is identified in each case by the fact that it advances in time as the rotation angle is increased from −30° to +40°.

In these and similar figures, each spatial position is shown by a separate waveform which is appropriately labeled (i.e., 40°) and shown separated in the "y" direction from other waveforms.

In the case of the 0.080-in. notch shown in FIG. 8, the amplitude of the 0° maximum amplitude return is sufficiently large to be peak detected and still be recognizably different from the background signals.

This is not the case for the 0.020-in. notch shown in FIG. 9. The apparently noisy signals are a result of the superpositon of many ultrasonic returns from the countersink region. The operator's ability to reliably detect a 0.020-in. notch has been considerably reduced, and no amount of conventional time signal averaging will improve the results. The only distinguishing feature of the defect 135b is the fact that it appears to walk when viewed on the A-scan display. In this invention, means are provided to predict the walk rate of a defect within the inspection zone.

Figure 5:
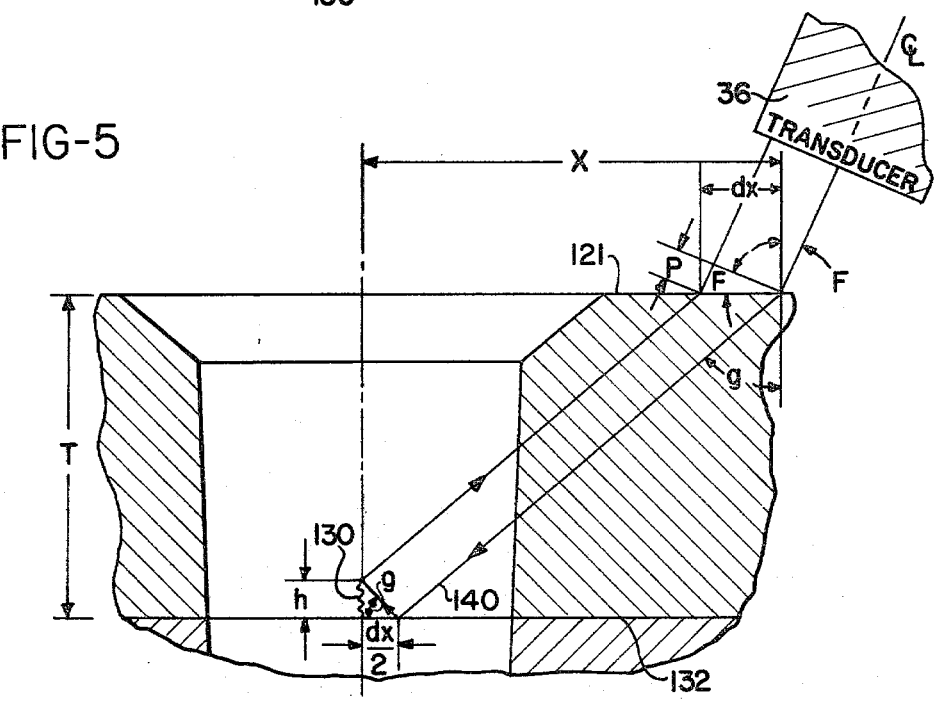
FIGS. 5-7 are ray traces illustrating the changes in geometry of the ultrasonic signal path as the transducer moves around a fastener.
Figure 6:
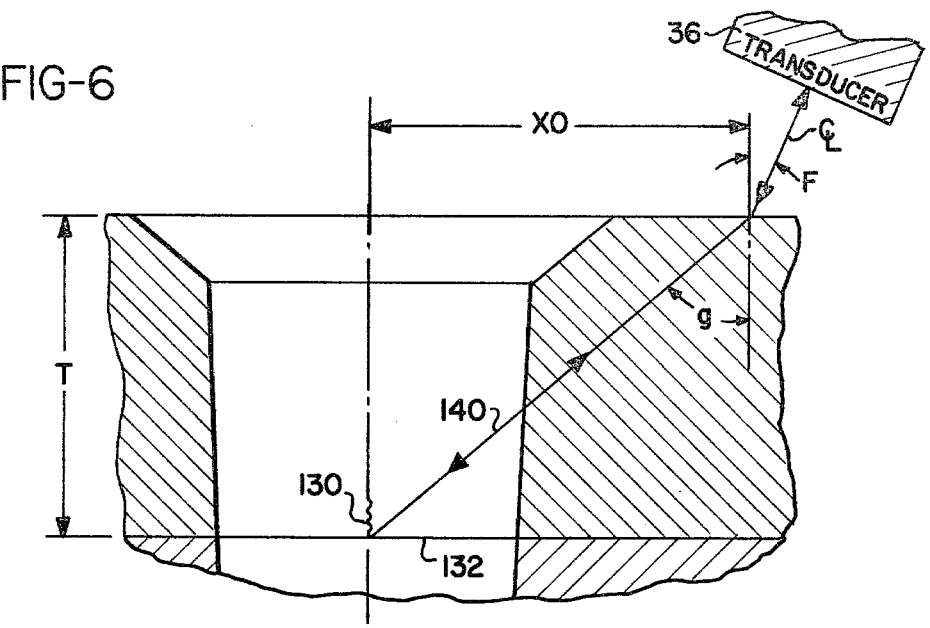
Figure 7:
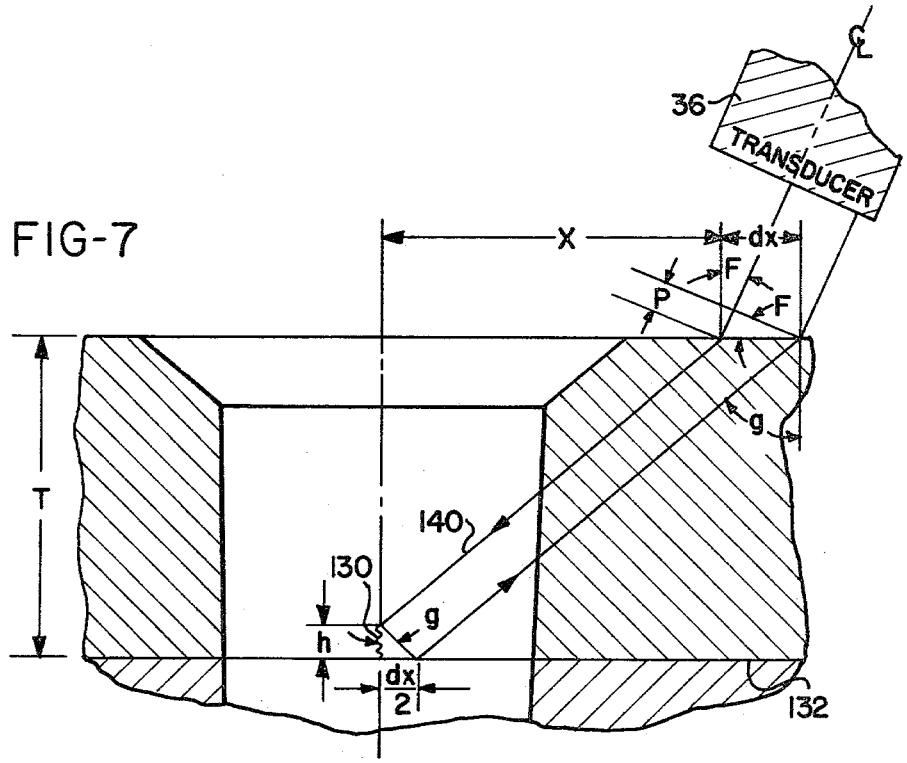

FIGS. 5–7 are ray traces showing the geometry of the faying-surface inspection zone about a tapered fastener. For clarity, this analysis is two-dimensional, and considers the transducer moving towards the fastener in the tangent plane. This approach inherently makes assumption in the analytic treatment which ignores smaller components in the signal resulting from a full three-dimensional analysis. This approach is justified by empirical results indicating the error is less than 5%.

The arrival time of the center ray 140 of a pulse changes as a function of the rotation angle due to variation in path length p. FIG. 5 illustrates the first time the crack 130 is in view. The path length is greater than the nominal path shown in FIG. 6 by the amount p. FIG. 7 illustrates the last time the crack is in view, and the path length has been shortened by the amount p.

The distance from the center point of the transducer 36 on the outer surface 121 to the center of the fastener is $$x = (T+h) \tan g \qquad (1)$$

where T is the outer-skin thickness and h the height above the faying surface 132 at which the defect reflects the central ray of the beam back to the transducer. The angle g is the refracted angle of the ultrasound beam as determined by the continuity conditions at the interface. The position $x_0$ is the x value at which the beam is reflected in and out of the material on the same path. $x_0$ is the point at which h=0 and also the point at which the maximum amplitude of the return pulse is obtained. The amount of beam translation after reflection is the quantity dx.

From the geometry at the faying surface as shown in FIGS. 5 or 7, it can be seen that $$dx = 2 h \tan g \qquad (2)$$

The value of x at $h=0$ is determined from expression (1) to be $$x_0 = T \tan g \qquad (3)$$

Expressions (2) and (3) can be substituted into expression (1), with the resulting solution for dx being $$dx = 2 (x - x_0) \qquad (4)$$

From the geometry in the water column region shown in FIGS. 5–7, $$p = dx \sin F \tag{5}$$

where F is the angle of incidence of the ultrasonic beam. If expression (4) is substituted into (5), the additional path length p as a function of x and F is shown to be $$p = 2(x - x_0) \sin F \tag{6}$$

The change in path length resulting from the displacement from position $x_1$ to $x_2$ will be $$Dp = 2(x_2 2_1) \sin F = 2 \, Dx \sin F \tag{7}$$

The change in arrival time Dt resulting from this change in path length Dp is given by $$Dt = Dp/c_w \tag{8}$$

where $c_w$ is the longitudinal wave velocity in the water. The linear walk rate $W_L = Dt/Dx$ can, therefore, be defined by $$W_L = (2/c_w) \sin F \tag{9}$$

If the approximation $Dx = (pi/180) - DY$ (DY in degrees) is made, the equivalent rotational expression is found to be $$W(r, F) = (pi/180)(2/c_w) \, r \sin F \tag{10}$$

The variable r is nominally equal to the fastener radius and represents the off-set from the center of the fastener to the point of tangency with the inspection circle.

Figure 10:
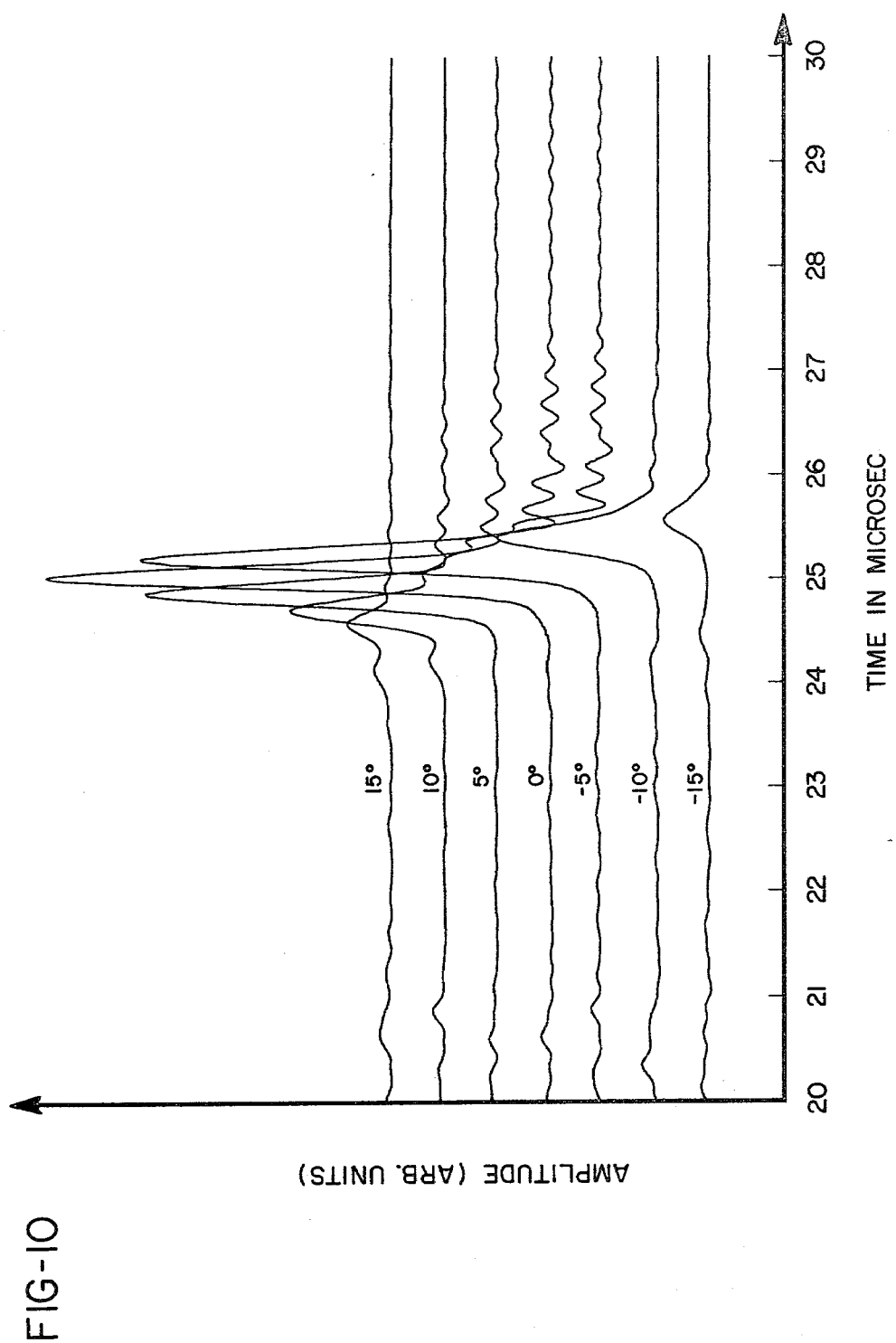
FIG. 10 illustrates an ultrasonic video A-scan return from a defect at the faying surface.

FIG. 10 illustrates an ultrasonic video A-scan response from a 0.055-in. quarter-penny fatigue crack extending radially from a ¼-in. tapered fastener at the faying surface of a 0.273-in. thick 2024-T4 aluminum outer panel. The angle of incidence F is 23°. The computed walk rate as defined by expression (10) is $W(r, F) = 35.11$ μsec./deg. The measured walk rate was determined to be 33.84 μsec./deg. with one standard deviation $s_w = \pm 1.38$ μsec./deg. and a regression coefficeint of $r^2 = 0.996$. Although there is a relative error of 3.6% between the computed and measured walk rate, the deviation is sufficiently small to justify using the approximate value for W(r, F) described by expression (10). For a range of fastener diameters from 3/16 in. to ½ in. and angle of incidence of 15° to 27°, the relative error never exceeded 5%.

The walk rate as defined by expression (10) is a constant for a given scan radius r and angle of incidence F. The time advance Dt introduced by rotation through an angle DY is defined by $$Dt = W(r, F) \, DY \tag{11}$$

The basic concept of the walking-gate spatial-averaging technique is to sample the video waveform every DY spatial increment for a full 360° rotation about a fastener, adding the sampled video waveforms together with the appropriate time delays introduced between waveforms to cause reinforcement of all defect indications advancing in time at walk rate W(r, F). Because W(r, F) varies as a function of r and F, it is necessary that either DY or Dt be varied to compensate for this effect. The time between sampling points of the video waveforms is also constrained by the Nyquist sampling criteria which requires that the sampling rate $f_N = 1/Dt$ be greater than twice the highest-frequency component present in the signal. For this reason it was decided that Dt would remain constant at $Dt = 0.1$ μsec delay between sampled waveforms. The spatial increment DY as function r and F then becomes $$DY(r, F) = (180/pi)(c_w \, Dt/2 \, r \sin F) \tag{12}$$

If an ultrasonic transducer is incremented about a fastener in DY steps as defined by expression (12), any defect present in the inspection zone defined by r and F will advance 1 Dt sample point per DY step.

FIG. 11a depicts the waveforms resulting from rotation about a fastener with a defect located at the 180° position on the fastener. For simplicity the defect indication is represented by a unit impulse with constant amplitudes as a function of angular position. The sampling gate is delayed by the time necessary to position the center of the gate ($t_p$) at the desired scan depth.

Hardware considerations dictate the maximum number of sample points M per waveform, but M is also chosen to be sufficiently large to handle the maximum walk length encountered. The number of waveforms $N = 360°/DY$ where DY is defined by expression (12). In this example DY is 45° which is only for demonstration purposes. Typically DY ranges from approximately 2° to 5° over the full range of panel thickness and fastener diameters. As can be seen from FIG. 11a, the unit impulse advances 1 DY point per DY step; and after 9 DY steps, a full 360° has been inspected.

FIG. 11b shows the incoming waveforms as they are added into a buffer memory. Each of the N waveforms is delayed by one memory address and added to the running total. The addition of a new N long sequence occurs every DY step, and only the running total is stored in buffer memory. After all N DY steps have been taken, the data-collection process is complete.

As can be seen in FIG. 11b, the first and last N-M buffer memory cells contain partial sums. Only the middle M memory cells have complete sums. The data collected at the 0 DY = 0° and 9 DY = 360° positions are identical. This implies that a wrap-around has occurred in the spatial sampling. If, as shown in FIG. 11c, the last N-M partial sums are added to the first N-M partial sums, all N buffer memory cells will now contain completed sums of M points each from the correct spatial positions as a result of the wrap-around effect.

FIG. 11c shows the complete set of a walking-gate data points in buffer memory; and, as can be seen, the defect indication is located at spatial position 6 DY = 270°. The peak signal occurs when the transducer is perpendicular to the defect, and the indication will appear at the center point of the sampling gate. This introduces a shift of $(M-1)/2$ address locations in buffer memory for all data points. Therefore, a circular shift to the left of $(M-1)/2$ location will bring the buffer memory into the proper order, with the defect indication appearing at 4 DY = 180° as shown in FIG. 11d. Because M is a constant for a given system, this circular shift need not actually be performed. The buffer memory array can remain unchanged, but the starting point of the array will be $(M-1)/2$ and the ending point will be $[(M-1)/2) - 1]$, with the point N falling between these two points. When data are transferred from buffer memory in either a CRT or plotter, the output will occur in this order.

The two final processing steps are the removal of the constant offset in the data, followed by the multiplication of each of the N points in the buffer-memory array by DY. Any time-stationary indications appearing at the same location in the sampling gate will be added in buffer memory and will appear in each of the N array points as a constant offset. To remove the offset, the array is scanned for the minimum value. This minimum value is then substracted from each of the N array points. The multiplication by DY effectively normalizes the array and compensates for the varying number of points N in the walking-gate array.

Figure 12:
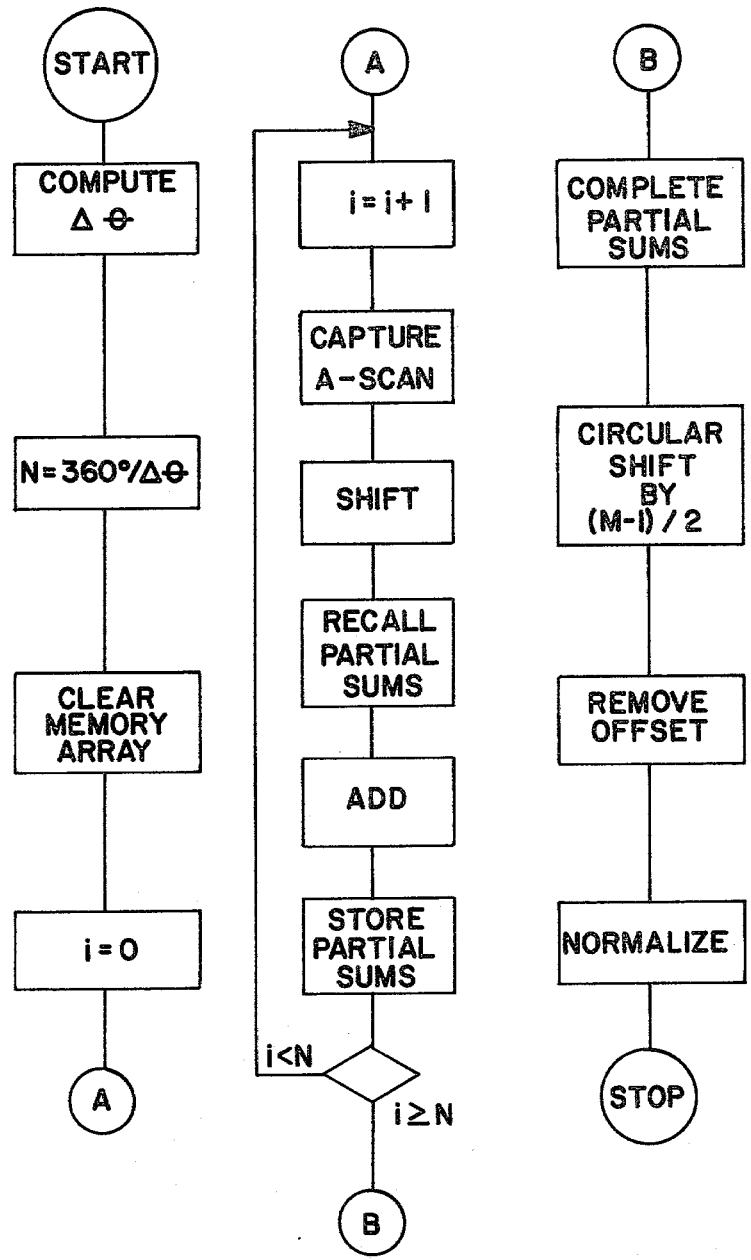
FIG. 12 is a flow chart illustrating the process used in this invention.

A summary of the walking-gate spatial-averaging technique is shown in the flow chart of FIG. 12.

To demonstrate and provide a better understanding of the effects of the walking-gate spatial-averaging signal processing on the variety of possible ultrasonic input waveforms, a computer model was constructed which incorporates the primary sources of interference. The model was designed to have multiple walking pulses with walk centers assigned at arbitrary Y locations. The walking pulses also had a Gaussian amplitude envelope which caused the pulse amplitude to rise and fall as a function of Y. The spatial-averaging increments, DY, were computed using function (12), but the actual walk rate of the pulse could be forced to deviate from the computed value by any desired amount. The two primary interference signals modeled were time-stationary or nonwalking pulses and additive Gaussian random noise. All pulses had variable widths and peak heights, and the magnitude of the standard deviation of the noise was controllable.

Figure 13:
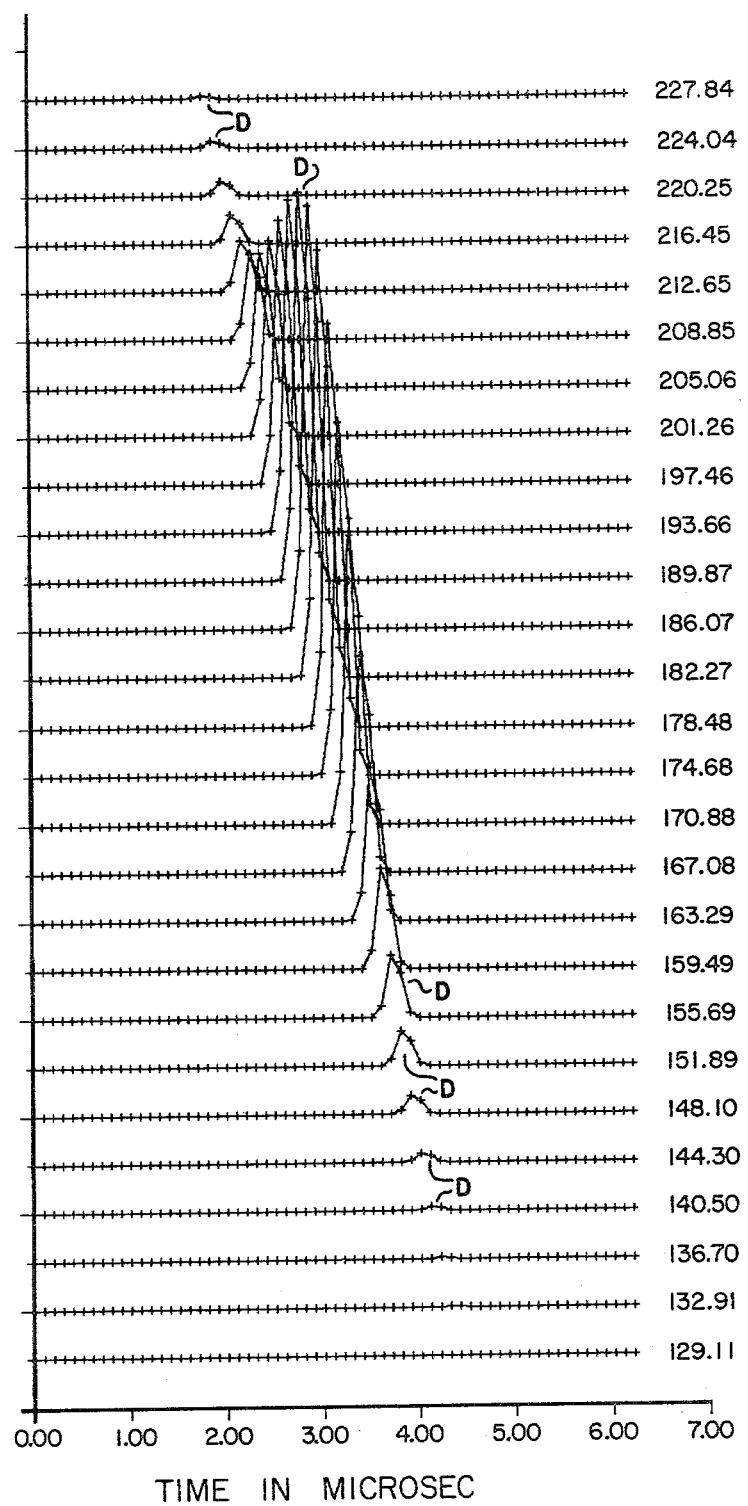
FIG. 13 represents a series of ultrasonic return pulses taken from different positions of a transducer relative to a theoretical defect located at the 180° position.

A plot of the input data for a typical walking pulse D centered at 180° is shown in FIG. 13. Each signal has a zero baseline, but is offset from the next waveform by a constant amount in order to permit better observation of the walking effect. The Y position is indicated to the right of each waveform with a DY increment of 3.8° between waveforms. Each (+) symbol indicates a sampled data point and there are M=63 data points per input signal. In FIG. 13, the input data shown covers only a range of approximately 100°.

Figure 14:
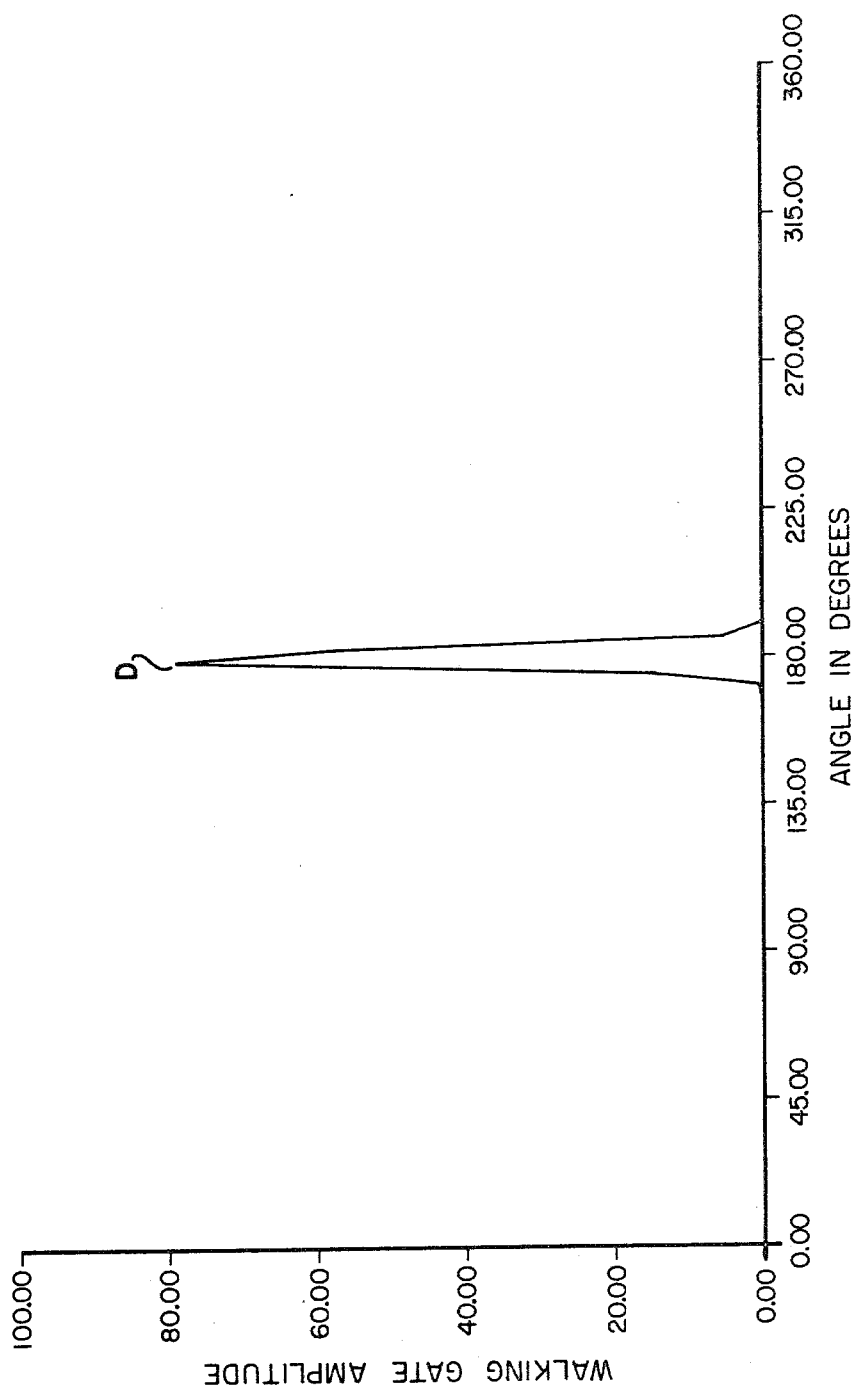
FIG. 14 illustrates the results of the spatial averaging technique as applied to the series of plots shown in FIG. 13.

FIG. 14 shows the result of the walking-gate spatial-averaging operation. The horizontal axis indicates the angular position of the transducer. Because the defect indications of the input data were visible for approximately 84°, a conventional peak-detected envelope would have been considerably wider in degrees than the indication shown in FIG. 14. This increase in spatial resolution is limited by the width of the ultrasonic pulse, and although it represents a substantial increase over the peak-detected system of A-1, it could be further improved if the system bandwidth were increased and if RF returns containing phase information rather than video-bandwidth-limited pulses were used.

In the example of FIG. 14, no attempt has been made to remove the offset constant from the processed output. As can be seen, if the input data have a zero baseline, and no time-stationary pulses the processed output will also have a zero baseline. This is not the case for data shown in FIG. 15.

Figure 15:
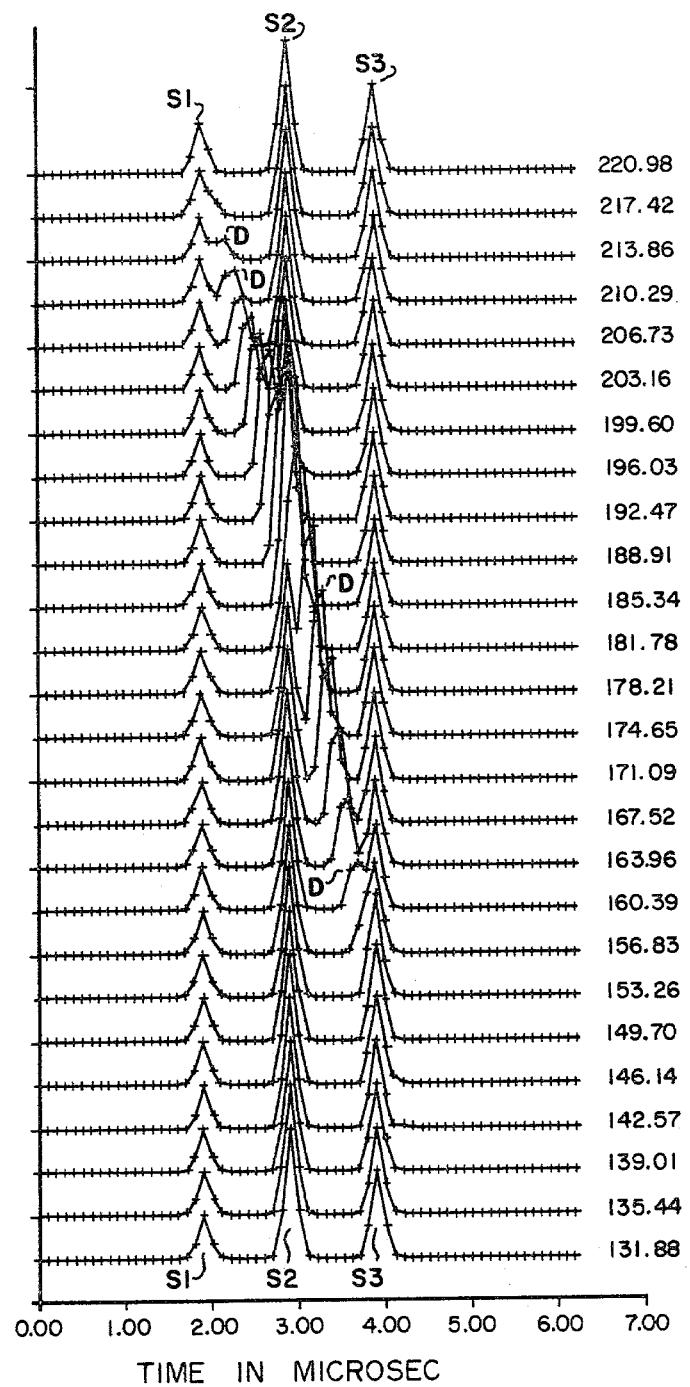
FIG. 15 represents a series of plots taken of a theoretical defect which appears to be moving through a field of three time-stationary returns.

FIG. 15 depicts a very small defect D indication walking through a field of three time-stationary pulses S1, S2, and S3. In a peak-detection system, this pulse would be virtually lost because the only period in which the amplitude of the walking pulse exceeds the amplitude of the stationary pulse is when the two reinforce at 180°.

Figure 16:
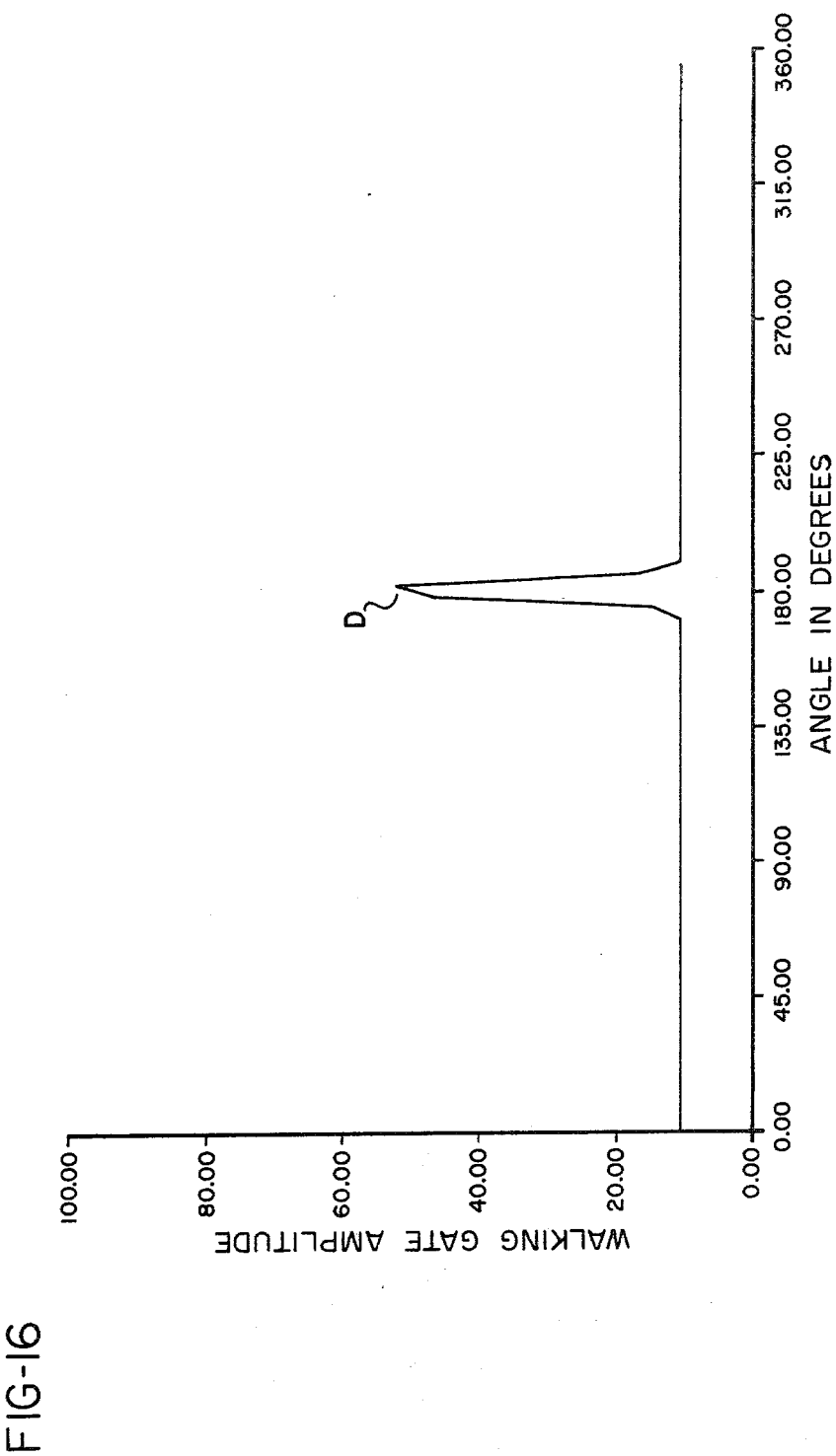
FIG. 16 illustrates the results of the spatial averaging technique as applied to the series of plots shown in FIG. 15

FIG. 16 shows the dramatic improvement which can be obtained when this signal-processing technique is used to distinguish walking from time-stationary returns. The constant offset term is the result of these time-stationary returns, and it can be shown that the magnitude of the offset constant is proportional to the integral of the time-stationary returns over the period of the sampling window.

Figure 17:
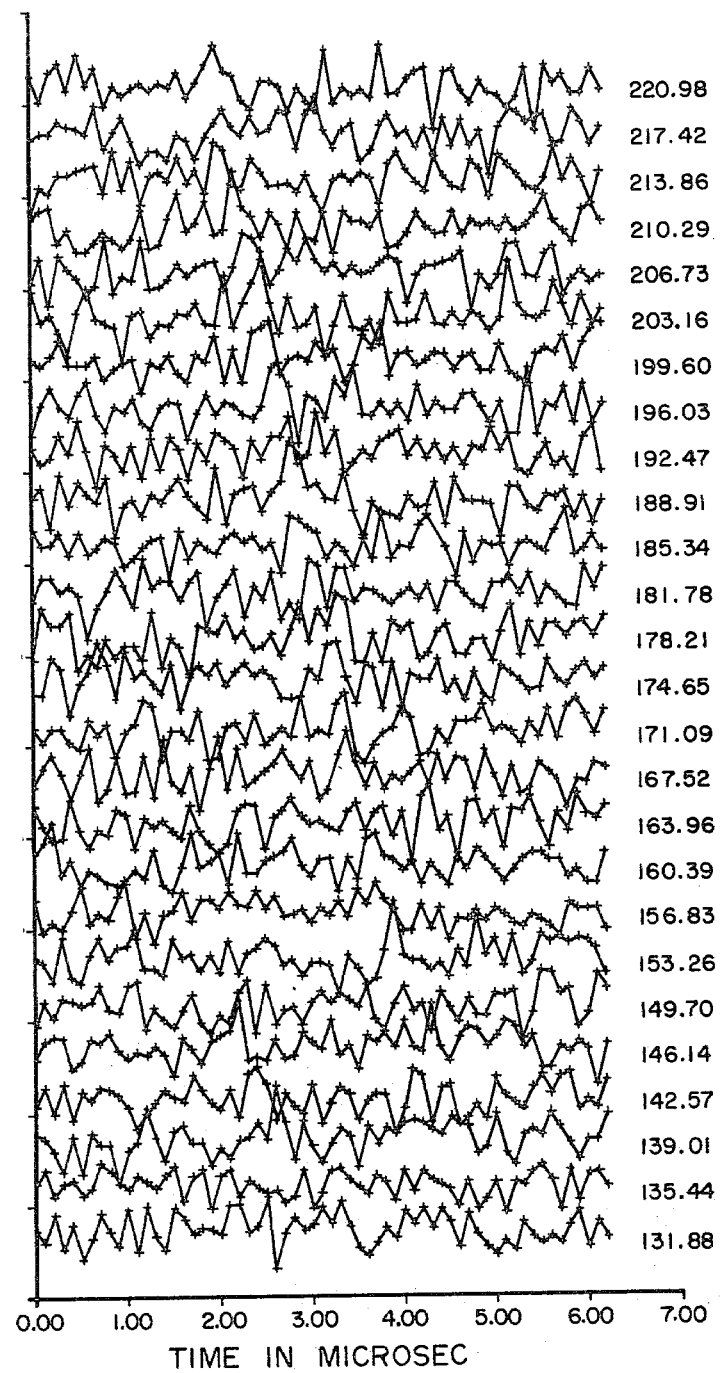
FIG. 17 is a series of plots illustrating a theoretical defect centered at 180° which is moving through Gaussion random noise.

FIG. 17 illustrates a pulse advancing in time through Gaussian random noise. The peak signal-to-noise ratio (S/N) is approximately 1. Because the pulse is advancing in time, conventional signal averaging would give no improvement in S/N.

Figure 18:
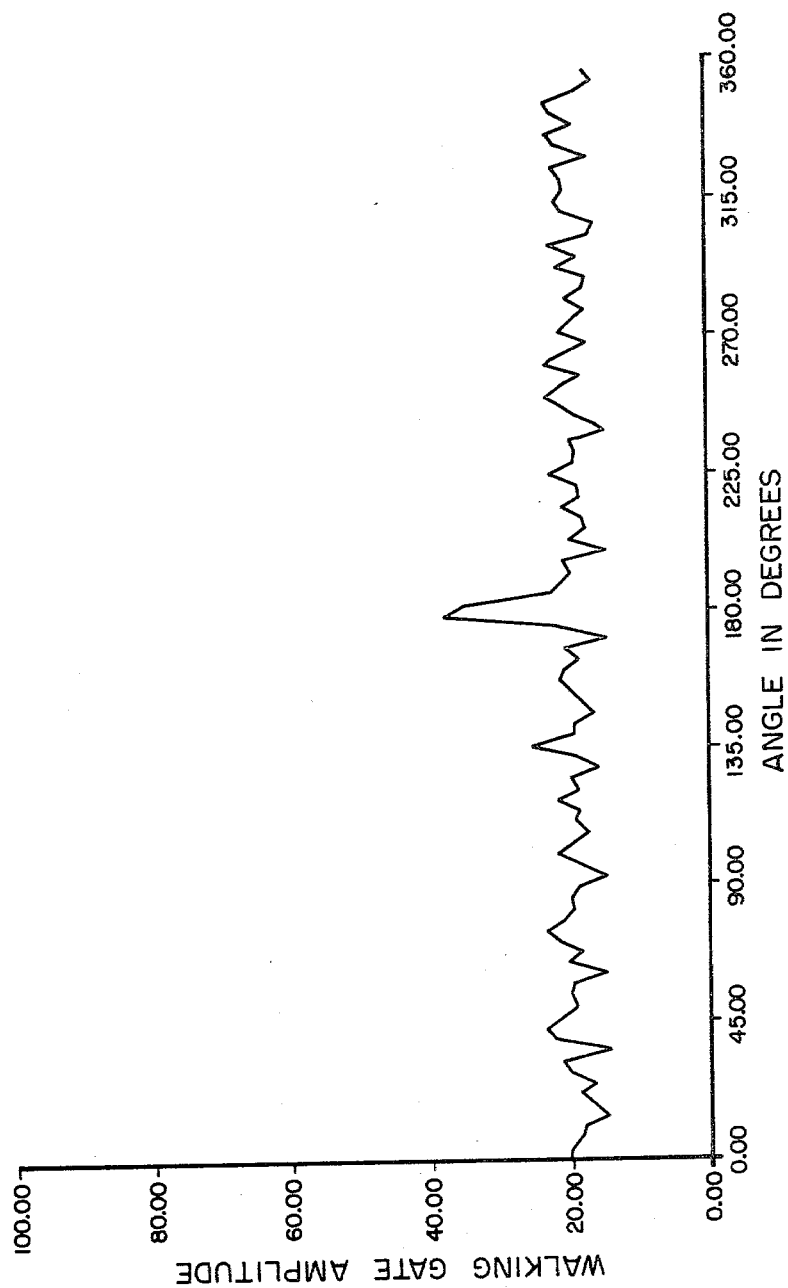
FIG. 18 illustrates the results of the spatial averaging technique as applied to the series of plots shown in FIG. 17.

As can be seen in FIG. 18, however, the walking-gate spatial-averaging technique is able to improve the S/N; and in this case with M=63, the improvement is approximately a factor of M=18 dB.

Figure 19:
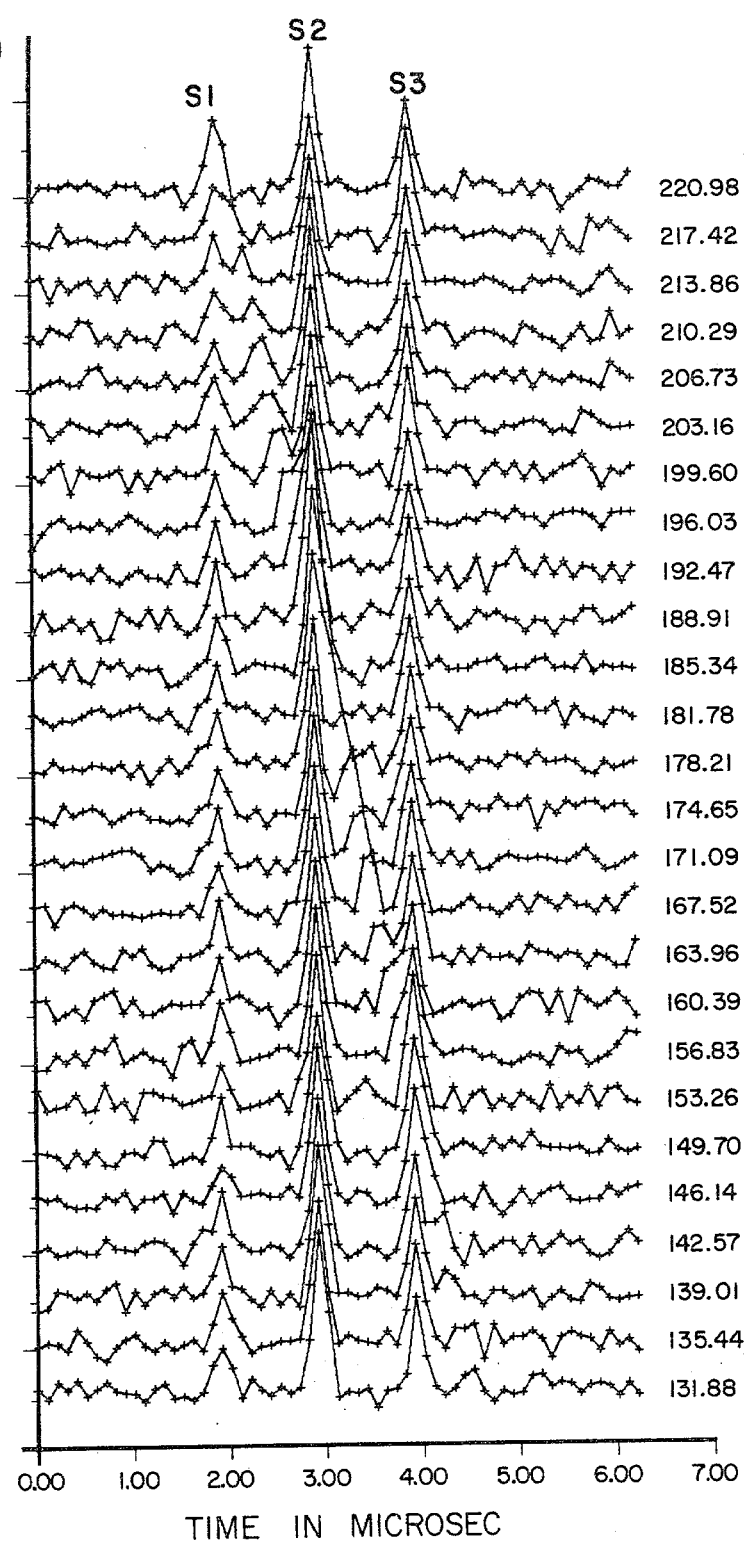
FIG. 19 is a series of plots of a theoretical defect moving with respect to both time-stationary signals and Gaussion random noise signals.

A composite input data set, consisting of both time-stationary S1, S2, and S3 signals and Gaussian random noise signals, is shown in FIG. 19. These input data are meant to be representative of typical countersink returns found in fastener inspections. The expected S/N improvement is demonstrated by the output signal shown in FIG. 20.

Figure 20:
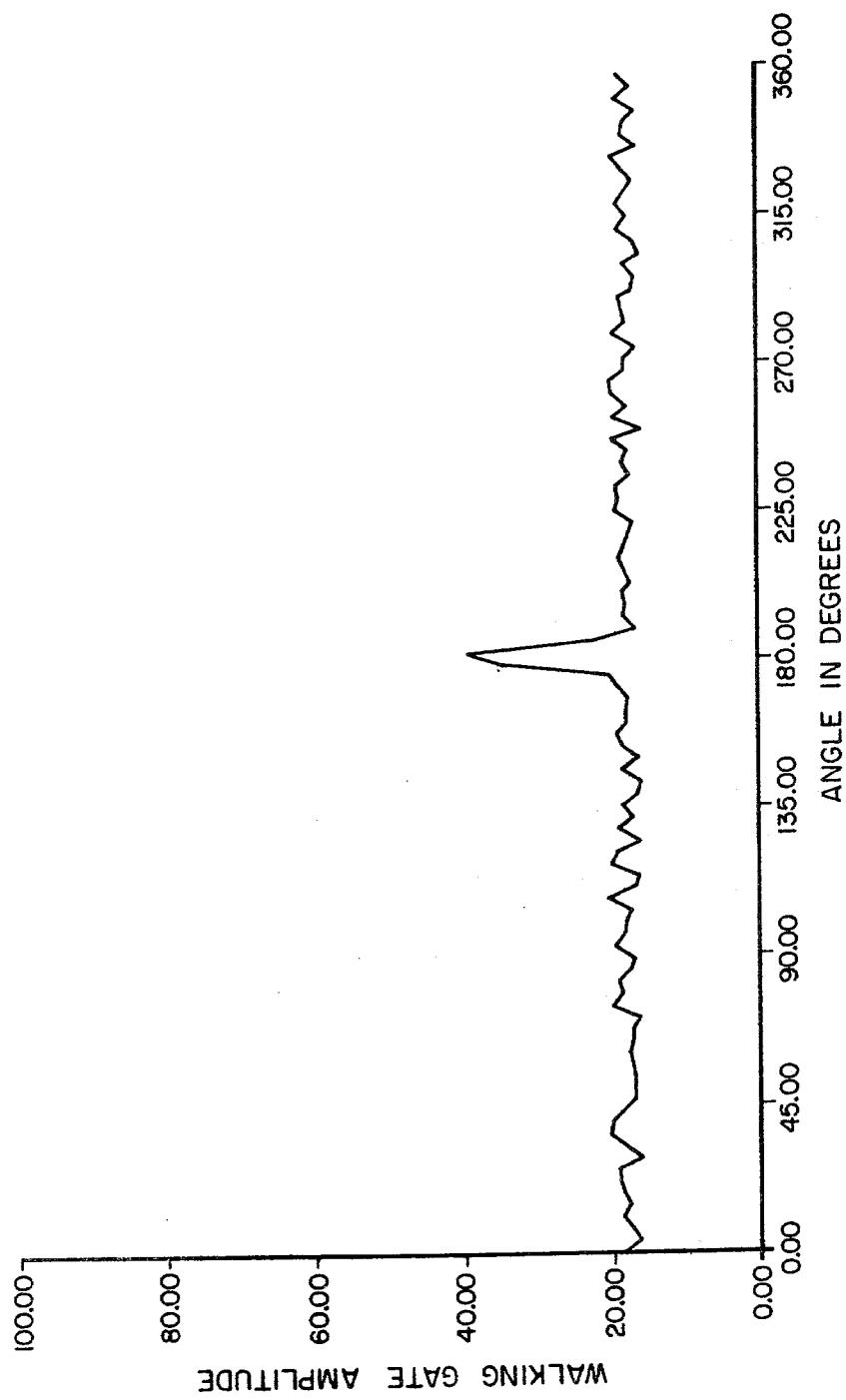
FIG. 20 illustrates the results of the spatial averaging technique as applied to the series of plots shown in FIG. 19.
Figure 21:
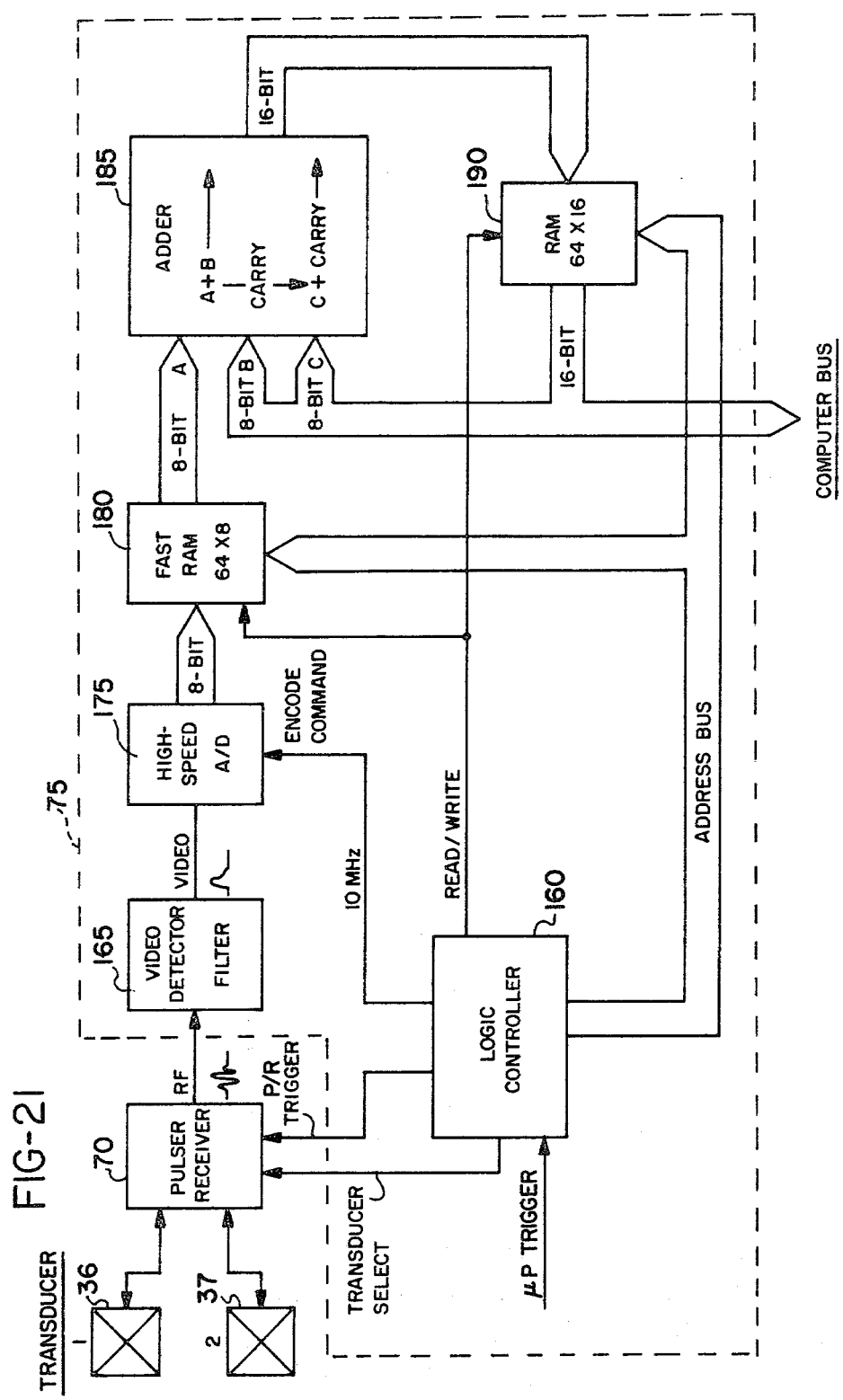
FIG. 21 is an electrical schematic diagram showing the transducers, the pulse receiver and the components which comprise the time averaging circuitry.

The implementation of the walking-gate spatial-averaging system in a field-usable scanner is shown in FIGS. 3, 20, 21, and includes the scanner 10 (with transducers 36, 37); a pulser/receiver (P/R) 70 sampling gate 75, a stepping-motor 100, a display 25, and a microcomputer (uP) control element 90.

The scanner 10 has two adjusting rings 55, 56 which select fastener diameter 2r and angle of incidence F of the ultrasonic transducer. Feedback elements attached to the adjustment rings input the current value of r and F to the microcomputer 90. From these inputs the microcomputer calculates and displays the fastener diameter and scan depth. The microcomputer 90 also calculates the delay time before the start of the sampling gate (the sampling gate is the source of the M=63 sampling point waveform described earlier) and the appropriate DY (r, F) spatial increment.

When the operator initiates a scan, the ultrasonic transducer 36 is stepped in N steps around the fastener, with the sampling gate presenting a new M-long waveform and the microcomputer performing the shift and add for each DY step. After a full 360° of rotation about the fastener, the microcomputer selects transducer 37 and performs the same process for the reverse rotation to the 0° home position. The microcomputer 90 then performs the remainder of the signal-processing steps outlined in FIG. 12 and superimposes the walking gate output on a circle with defect indication extending outward for transducer 36 and inward for transducer 37.

The circular display is then output by direct-memory access (DMA) from the microcomputer random-access memory (RAM) to the x and y inputs of the CRT display 25. The complete scan sequence required approximately 15 sec. in each direction of rotation and another 1 sec. before the display appears reduced to a single console plus scanner.

FIG. 20 shows the sampling gate 75 used in the preferred embodiment of the invention. The sampling gate 75 is a time averaging circuit operated under the control of the microprocessor 90 and which activates the transducers 36, 37 to generate a plurality of ultrasonic pulses each time the transducers have moved a DY step.

The transducers 36, 37 are connected directly to the pulser receiver 70, and they are pulsed under the control of a logic controller circuit 160 which has a trigger input from the microprocessor 90. The logic controller 160 also selects which transducer is to be pulsed.

The ultrasonic echoes are processed by the pulser receiver and directed into a video detector and filter circuit 165. The signal is a video signal, and the filter band limits the signal consistent with the sampling rate. This filtered signal is then directed to a high-speed A/D 170 which converts the amplitude of the video signal into an 8-bit number. In the preferred embodiment, the high-speed A/D is a Model MATV-0816 manufactured by Computer Labs, Inc.

There are 64 samples made of each input signal, and these are stored in a 64×8 fast RAM 180. This data is applied through an adder circuit 180 and accumulated in a 64×16 RAM 190. The RAM 190 will accept up to 256 input signals, however, in the preferred embodiment, only 100 pulses are made at each D/Y position. The resulting signal in RAM 190 is therefore a time-averaged signal having a S/N improvement of approximately 24 dB which is then passed to the microprocessor for spatial signal averaging.

Figure 22:
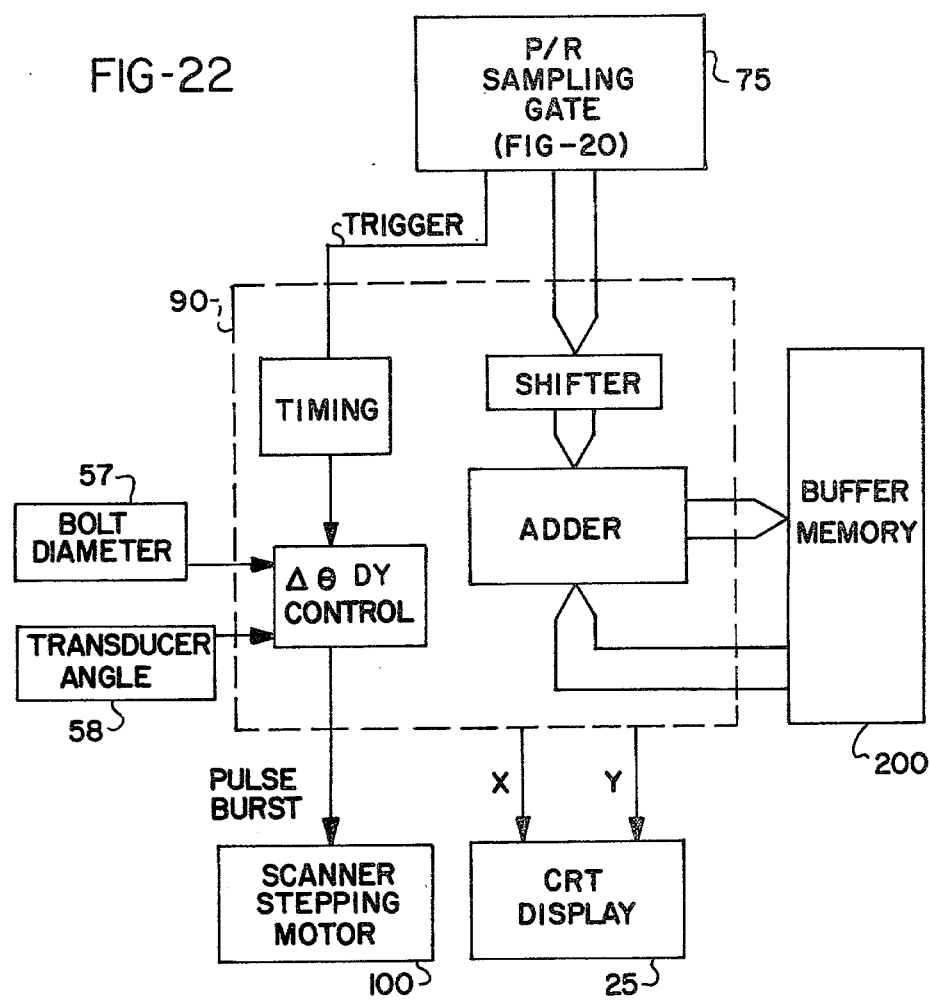
FIG. 22 is an electrical block diagram of the spatial averaging circuitry of this invention.

The microcomputer 90 shown in FIG. 22 then initiates a DY step and, during the 36-msec settling time, adds the input waveform into the microcomputer RAM or buffer 200 and advances an index register, pointing to the starting location of the addition process, by 1. The microcomputer then initiates a clear of the sampler RAM, and the sequence begins again and continues for N DY steps.

All further signal processing, calculation, control, and display functions are performed by the Intel 8080A microcomputer at the slower microcomputer speeds.

The scanner utilizes ten-turn potentiometers 57, 58 for r and F feedback to the microcomputer 90. The size of the DY steps is computed from these input values. In order to generate a variable-size DY(r, F) step, a high-resolution stepping motor 100 is used which is capable of moving through a constant step of $DY_o = 0.1125°$. The microcomputer then computes the integer number of $DY_o$ steps to be taken in order to move through the spatial increment DY(r, F). The rounded-off integer number of steps is expressed as $$n(r,F) = INT[DY(r,F)/DY_o + 0.5] \quad (13)$$

if expression (12) is substituted into (13) with $Dt = 0.1$ usec and $DY_o = 0.1125°$, $$n(r,F) = INT[1.4838/r \sin F) + 0.5)] \quad (14)$$

The fractional portion of a $DY_o$ step can be recovered by taking additional or fewer $DY_o$ steps whenever the error accumulates to an integer number.

The stepping motor 100 used in this invention is manufactured by Mesur-Matic Electronics Corp. The unit was gear reduced by a factor of four to achieve the desired torque/speed capability and $DY_o$ step size.

The following program listing was developed for use in connection with the preferred embodiment of the invention discribed above:

```
            LXI  H, 08000H
            SHLD 05104H
            LXI  H, 09000H
            SHLD 05100H
            LXI  H, 0A000H
            SHLD 05102H
            XRA  A
            MOV  C, A
            MVI  A, 000A3H
ZERO:       MOV  M, C
            INX  H
            CMP  H
            JNZ  01C16         ;ZERO OUT ARRAY
SGC:        LDA  07206H        ;LOAD DATA FOR START GATE COUNTER
            OUT  02            ;LOW ORDER BITS
            LDA  07207H
            OUT  03            ;HIGH ORDER BITS
            NOP
            NOP
            NOP
            NOP
            NOP
            NOP
START:      LDA  07200H        ;NUMBER OF PULSES PER CLOCK PULSE
            MOV  C, A
PULSE:      MVI  A, 000FEH     ;PULSE THE TRANSDUCER
            OUT  00
            NOP
            NOP
            NOP
            NOP
            MVI  A, 000FFH
            OUT  00
LOOP:       IN   00            ;CHECK SWEEP STATUS
            ANI  01
```

```
            JZ 01C38H          ;LOOP
            DCR C              ;NEED MORE PULSES?
            JNZ 01C30H         ;YES, JUMP TO PULSE
            MVI B,000F8H       ;SET COUNTER FOR NUMBER OF SAMPLES
            JMP 01C60H         ;CONTINUE
            NOP

EXTRD:      MVI A,000FDH
            OUT 00
            MVI A,000FFH
            OUT 00
            JMP 01C2CH         ;START

CONT:       LHLD 05102H
CONT0:      XCHG
CONT1:      LHLD 05100H
            MVI A,000FDH       ;CLOCK READ DATA PULSE
            OUT 00
            IN 02              ;INPUT LOW ORDER BITS OF DATA
            NOP
            MOV M,A            ;STORE AT H
            IN 03              ;INPUT HIGH ORDER BITS OF DATA
            NOP
            INX H
            MOV M,A            ;STORE AT H +1
            MVI A, 000FFH      ;TURN OFF READ DATA PULSE
            OUT 00
            XRA A              ;ZERO OUT NEXT TWO LOCATIONS FOR
            INX H              ;FLOATING POINT CONVERSION
            MOV M,A
            INX H
            MOV M,A
            CALL 013BEH        ;CONVERT TO FLOATING POINT THROUGH
            JMP 01C90H         ;HIGH SPEED MATH BOARD

RESUME:     LHLD 5100
            LDAX D             ;STORE THE FLOATING POINT VALUE OF THE
            MOV M,A            ;THE DATA (REPEAT FOR 4 LOCATIONS OF FLOATING
            INX H              ;POINT NUMBER)
            INX D
            LDAX D
            MOV M,A
            INX H
            INX D
            LDAX D
            MOV M,A
            INX H
            LDAX D
            MOV M,A
            INX D              ;DE=POINTER TO NEXT AVAILABLE LOCATION
            MOV A,E
            CPI 000FCH         ;CHECK FOR END OF A0 TABLE
            JZ 01CAFH          ;END
            CALL 013AAH        ;SUMS PREVIOUS VALUE
            MVI A, 04
            CMP E
            JZ 01D20H          ;IF FIRST SAMPLE IT STORES VALUE IN B1 TABLE
END:        LHLD 05102H
            LDA 09000H         ;HL=NEW POINTER TO A0 MEMORY
            MOV M,A
            INX H
            LDA 09001H         ;STORES SUM IN SHIFTED A0 TABLE
            MOV M,A
            INX H              ;(REPEAT FOR 4 LOCATIONS OF SUM)
```

```
              LDA 09002H
              MOV M,A
              INX H
              LDA 09003H
              MOV M,A
              INX H
              MOV A,L
              CMP B                 ;CHECKS FOR END OF AO TABLE
              SHLD 05102H
              JNZ 01C64H            ;(CONT1) CONTINUE COLLECTING DATA
              LXI H,0A000H
              SHLD 05102H           ;RESETS POINTER TO BEGINNING
              JMP 01C50H            ;START
CONVERT:      LXI B, 08000H
              LXI H,08000H
              XCHG
BEGIN:        LHLD 05100H           ;THIS ROUTINE CONVERTS ALL THE VALUES
              LDAX D                ;(AVERAGES) IN THE BI MEMORY TABLE FROM
              MOV M,A               ;FLOATING POINT TO FIXED POINT
              INX D
              INX H
              LDAX D
              MOV M,A
              INX D
              INX H
              LDAX D
              MOV M,A
              INX D
              INX H
              LDAX D
              MOV M,A
              INX D
              CALL 01DF0H           ;AVG
              CALL 013C3H           ;FIXSD
              LHLD 05100H
              MOV A,M
              STAX B
              INX H
              INX B
              MOV A,M
              STAX B
              INX H
              INX B
              MOV A,M
              STAX B
              INX H
              INX B
              MOV A,M
              STAX B
              INX B
              MVI A,00082H
              CMP B
              JNZ 01CDEH            ;BEGIN
              MVI A, 000D0H
              CMP C
              JNZ 01CDEH            ;BEGIN
              RET
BIMEM:        XCHG                  ;HL=POINTER TO AO TABLE
              SHLD 05106H
              LHLD 05100H           ;HL=POINTER TO MATH BOARD
              XCHG                  ;DE=POINTER TO MATH BOARD
              LHLD 05104H           ;HL=POINTER TO BI MEM TABLE
              LDAX D
              MOV M,A
              INX D
              INX H                 ;STORES TO AO VALUE THAT IS SHIFTED
```

```
            LDAX D              ;OUT INTO THE BI MEM TABLE
            MOV M,A
            INX D
            INX H
            LDAX D
            MOV M,A
            INX D
            INX H
            LDAX D
            MOV M,A
            INX D
            MVI A, 00082H
            CMP H
            JNZ 01D46H          ;REST
            MVI A, 000D0H
            CMP L
            JZ 01D50H           ;WRAP
EX
WRAP:       LXI H,08000H
            SHLD 05104H         ;POINTER TO BI MEM TABLE
            SHLD 05106H
            LXI H,0A004H
            SHLD 05102H         ;POINTER T AO TABLE
            LXI H,09000H
            SHLD 05100H         ;POINTER TO MATH BOARD
            LHLD 05100H
            XCHG                ;DE=POINTER TO MATH BOARD
            LHLD 05104H         ;HL= POINTER TO BI MEM TABLE
            MOV A,M
            STAX D
            INX D
            INX H
            MOV A,M
            STAX D
            INX D
            INX H
            MOV A,M
            STAX D
            INX D
            INX H
            SHLD 05104H
            LHLD 05102H
            MOV A,M
            STAX D
            INX D
            INX H
            MOV A,M
            STAX D
            INX D
            INX H
            MOV A,M
            STAX D
            INX D
            INX H
            MOV A,M
            STAX D
            INX H
            SHLD 05102H         ;THE VALUES IN THE FINAL 64
            CALL 013AAH         ;SAMPLES IN AO MEMOORY ARE ADDED
            LHLD 05100H         ;TO THE BEGINNING 64 BI MEM VALUES
            XCHG                ;WHICH ARE PARTIAL SUMS.
            LHLD 05106H         ;THIS LEVELS THE VALUES IN THE
            LDAX D              ;ENTIRE BI MEM TABLE.
            MOV M,A
            INX D
            INX H
```

```
            LDAX D
            MOV M,A
            INX D
            INX H
            LDAX D
            MOV M,A
            INX D
            INX H
            LDAX D
            MOV M,A
            INX H
            SHLD 05106H
            INX D
            INX H
            LDAX D
            MOV M,A
            INX D
            INX H
            LDAX D
            MOV M,A
            INX D
            INX H
            LDAX D
            MOV M,A
            INX H
            SHLD 05106H
            MOV A,L
            CPI FC
            JZ 01DC0H          ;CHECKS FOR END OF A0 MEMORY CONVERT
            JMP 01D65          ;B1 MEM FROM FLOAT POINT TO FIXED POINT
CONV:       LDA 07200H
            STA 09000H
            XRA A
            STA 09001H
            STA 09002H
            STA 09003H
            CALL 013BEH
            LHLD 09000H
            SHLD 050D8H
            LHLD 09002H
            SHLD 050DAH
            JNZ 01E00H         ;CONVRT
            LHLD 050D8H
            SHLD 09004H
            LHLD 050DA
            SHLD 09006H
            CALL 013A5         ;FDIV
            RET

CONVRT:     MVI A, 0003FH
            STA 09000H
            XRA A
            STA 09001H
            STA 09002H
            STA 09003H
            CALL 013BEH        ;FLTDS
            LHLD 050D8H
            SHLD 09004H
            LHLD 050DAH
            SHLD 09006H
            CALL 013A0H
            LHLD 09000H
            SHLD 050D8H
            LHLD 09002H
            SHLD 050DAH
            JMP 01CD7H         ;CONVERT
```

The stepping-motor approach for determining the spatial increments is a possible limitation to extension of this signal-processing technique into other applications. An alternate approach may be to use continuous rotation with the P/R being triggered at the appropriate spatial positions. With this approach, only position feedback in conjunction with the sampling gate and microcomputer controller will be required for interface of this system with conventional ultrasonic-scanning equipment.

It is also possible to apply this system in cases where the walking signal occurs periodically with an unknown position dependence. In such a case, the walk rate would be scanned and the microcomputer would lock onto the optimum signal condition. In this way it may be possible to remove multiple reflection from some normal-incidence scanning geometries.

Any linear or polar shear-wave inspection presently being performed with conventional C-scan equipment can be accomplished using walking-gate spatial-averaging with a significant improvement in S/N and spatial resolution. Only the walk-rate function would require modification, and this would be strictly a software change. Inspection of tubing or pipe for radial fatigue cracks is another possible area which might benefit from this signal-processing technique.

While the method herein described, and the form of apparatus for carrying it into effect, constitute preferred embodiments of this invention, it is to be understood that the invention is not limited thereto, and that changes may be made therein without departing from the scope of the invention.

What is claimed is:

1. A method of detecting flaws within solid material ultrasonically comprising the steps of positioning a transducer relative to suspected flaws and transmitting an ultrasonic pulse beam into the material under test, detecting reflected ultrasonic signals within a time period when suspected flaw signals are likely to be returned, dividing the detected signals within said time period into a plurality of segments and measuring the amplitude of each segment, adding a number representing the amplitude of the detected signal for each segment into individual memories, thereafter moving said transducer through an incremental distance such that the transit time of the ultrasonic signal is shortened or lengthened by one time segment with respect to a given spatial location within said material, and then transmitting another pulse into said material, accumulating the numbers representing the amplitude of the detected signal for each segment into said memories after the relative position of said segments and said memories has been shifted in the direction related to the movement of said transducer, repeating the above steps until the transducer has traversed the area of suspected flaws whereby signals received within said time period relating to given spatial locations are accumulated in the memories, and thereafter reading the memories to obtain information regarding the location and magnitude of any flaws within the material.

2. Apparatus for the ultrasonic detection of flaws located within solid material, said apparatus including transducer means positioned at an acute angle to the surface for transmitting a narrow beam of ultrasonic energy into the material and for receiving signals reflected from within the material, means for moving said transducer relative to the surface of the material, means for sensing the signals received by said transducer means within the limited period of time reflected signals from flaws within the material are likely to occur, means for dividing said received signals within said period of time into a plurality of equally spaced segments means for causing said transducer to transmit pulses of ultrasonic energy each time said transducer moves through an increment of distance represented by one of said segments, a plurality of memory means responsive to said transducer means for storing representations of the amplitude of the received signals within each of said segments, means for adding the representations of amplitude of the received signals into corresponding memories within said memory means, and means for interrogating said memories after said transducer has traversed the suspected flaw locations to determine the spatial locations of any flaws detected.

3. Apparatus for ultrasonic detection of flaws located within solid material, said apparatus including transducer means for transmitting a beam of ultrasonic energy into the material and for receiving signals reflected from within the material, which can be positioned at various angular and positional coordinates on the surface of said material, means for indexing said transducer over the surface of the material, such that suspected defect areas are scanned, means for sensing the angular and positional coordinates of said transducer means referenced to said material geometry, means for sensing reflected signals received by said transducer within a limited period of time, means for dividing said received signals within said period of time into a plurality of equally spaced segments, means for causing said transducer to transmit a pulse or series of pulses each time the transducer indexes, a plurality of memory means for storing said received signals and said angular and positional coordinates, means for adding the representations of amplitude of the received signals from said time segments in such a manner that all ultrasonic signals received during a scan which are reflected from a small specific spacial volume within the material are summed together and stored in memory, means for interrogating said memories after said transducer has scanned the suspected flaw locations and extracting the summed flaw amplitudes and the location of such flaws referenced to the material geometry, means for displaying and/or transmitting to external devices said summed flaw amplitudes and location.

4. Apparatus for the ultrasonic detection of flaws located within solid material, said apparatus including transducer means positioned at an acute angle to the surface for transmitting a narrow beam of ultrasonic energy into the material and for receiving signals reflected from within the material, means for moving said transducer on the surface of the material, means for detecting the positional coordinates of said transducer referenced to said material, means for sensing reflected signals from flaws received by said transducers within a limited period of time, said period of time corresponding to a specific region within the material, means for dividing said received signals within said period of time into a plurality of equally spaced segments means for causing said transducer to transmit a pulse of ultrasonic energy each time said transducer moves through an increment of distance represented by one of said segments, a plurality of memory means responsive to said transducer means for storing representations of the amplitude of the received signals within each of said time segments, means for adding the representations of amplitude of the received signals from said time segments in such a manner that all signals received from a small local region of the material are summed together, means for interrogating said memories after said transducer has traversed the suspected flaw locations to determine the locations of any flaws detected.

* * * * *

UNITED STATES PATENT AND TRADEMARK OFFICE
CERTIFICATE OF CORRECTION

PATENT NO. : 4,292,848
DATED : October 6, 1981
INVENTOR(S) : J. Montgomery Raney and Francis M. Taylor It is certified that error appears in the above—identified patent and that said Letters Patent is hereby corrected as shown below:

The name of the first inventor "J. Montgomery Rainey" should be --J. Montgomery Raney--.

Col. 5, line 60, "countersilk" should be --countersink--.

Col. 7, line 14, "$Dp=2(x_2 2_1) \sin F = 2 Dx \sin F$" should be --$Dp=2(x_2-x_1) \sin F = 2 Dx^2 \sin F$--.

Signed and Sealed this

Thirtieth Day of March 1982

[SEAL]

Attest:

GERALD J. MOSSINGHOFF

*Attesting Officer*  *Commissioner of Patents and Trademarks*